US011000212B2

(12) United States Patent
Joseph et al.

(10) Patent No.: US 11,000,212 B2
(45) Date of Patent: *May 11, 2021

(54) ACOUSTIC SENSOR AND VENTILATION MONITORING SYSTEM

(71) Applicants: Thomas Jefferson University, Philadelphia, PA (US); RTM Vital Signs LLC, Fort Washington, PA (US)

(72) Inventors: Jeffrey I Joseph, Penn Valley, PA (US); Noud Van Helmond, Philadelpha, PA (US); Marc C Torjman, South Hampton, PA (US); Denise L Devine, Media, PA (US); Nance K Dicciani, Fort Washington, PA (US); Channy Loeum, Philadelphia, PA (US)

(73) Assignees: Thomas Jefferson University, Philadelphia, PA (US); RTM Vital Signs LLC, Fort Washington, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/995,912

(22) Filed: Aug. 18, 2020

(65) Prior Publication Data

US 2020/0375502 A1 Dec. 3, 2020

Related U.S. Application Data

(63) Continuation of application No. 16/544,033, filed on Aug. 19, 2019, now Pat. No. 10,881,330.
(Continued)

(51) Int. Cl.
*A61B 5/113* (2006.01)
*A61B 5/00* (2006.01)
(Continued)

(52) U.S. Cl.
CPC ............ *A61B 5/113* (2013.01); *A61B 5/0006* (2013.01); *A61B 5/022* (2013.01); *A61B 5/0816* (2013.01);
(Continued)

(58) Field of Classification Search
CPC ..... A61B 5/113; A61B 5/0816; A61B 5/4818; A61B 5/7282; A61B 7/003
See application file for complete search history.

(56) References Cited

U.S. PATENT DOCUMENTS 7,539,533 B2   5/2009   Tran
7,558,622 B2   7/2009   Tran
(Continued)

OTHER PUBLICATIONS

Boyd, et al., Effective Apnea-Hypopnea Index ("Effective AHI"): A New Measure of Effectiveness for Positive Airway Pressure Therapy, 2016, Sleep, vol. 39, No. 11, p. 1961-1970. (Year: 2016).*
(Continued)

*Primary Examiner* — Daniel L Cerioni
*Assistant Examiner* — Raymond P Dulman
(74) *Attorney, Agent, or Firm* — Christopher & Weisberg, P.A.

(57) ABSTRACT

A method of monitoring respiration with an acoustic measurement device, the acoustic measurement device having a sound transducer, the sound transducer configured to measure sound associated with airflow through a mammalian trachea, the method includes correlating the measured sound into a measurement of tidal volume and generating at least one from the group consisting of an alert and an alarm if the measured tidal volume falls outside of a predetermined range.

12 Claims, 11 Drawing Sheets

Related U.S. Application Data

(60) Provisional application No. 62/857,963, filed on Jun. 6, 2019, provisional application No. 62/719,918, filed on Aug. 20, 2018.

(51) Int. Cl.
  *A61B 5/022* (2006.01)
  *A61B 5/08* (2006.01)
  *A61B 7/00* (2006.01)
  *A61B 5/318* (2021.01)

(52) U.S. Cl.
  CPC .......... *A61B 5/1135* (2013.01); *A61B 5/4818* (2013.01); *A61B 5/7282* (2013.01); *A61B 7/003* (2013.01); *A61B 5/318* (2021.01); *A61B 5/4806* (2013.01); *A61B 5/681* (2013.01)

(56) References Cited

U.S. PATENT DOCUMENTS

| | | |
|---|---|---|
| 7,733,224 B2 | 6/2010 | Tran |
| 7,764,996 B2 | 7/2010 | Zhang et al. |
| 7,787,946 B2 | 8/2010 | Stahmann et al. |
| 8,005,540 B2 | 8/2011 | Zhang et al. |
| 8,032,206 B1 | 10/2011 | Farazi et al. |
| 8,103,333 B2 | 1/2012 | Tran |
| 8,104,470 B2 | 1/2012 | Lee et al. |
| 8,108,036 B2 | 1/2012 | Tran |
| 8,177,724 B2 | 5/2012 | Derchak et al. |
| 8,323,188 B2 | 12/2012 | Tran |
| 8,401,636 B2 | 3/2013 | Zhang et al. |
| 8,449,471 B2 | 5/2013 | Tran |
| 8,461,988 B2 | 6/2013 | Tran |
| 8,475,371 B2 | 7/2013 | Derchak et al. |
| 8,522,779 B2 | 9/2013 | Lee et al. |
| 8,525,673 B2 | 9/2013 | Tran |
| 8,525,687 B2 | 9/2013 | Tran |
| 8,531,291 B2 | 9/2013 | Tran |
| 8,626,292 B2 | 1/2014 | McCabe et al. |
| 8,634,915 B2 | 1/2014 | McCabe et al. |
| 8,680,991 B2 | 3/2014 | Tran |
| 8,684,900 B2 | 4/2014 | Tran |
| 8,690,799 B2 | 4/2014 | Telfort et al. |
| 8,702,627 B2 | 4/2014 | Telfort et al. |
| 8,715,206 B2 | 5/2014 | Telfort et al. |
| 8,747,336 B2 | 6/2014 | Tran |
| 8,755,535 B2 | 6/2014 | Telfort et al. |
| 8,762,733 B2 | 6/2014 | Derchak et al. |
| 8,764,651 B2 | 7/2014 | Tran |
| 8,805,493 B2 | 8/2014 | Zhang et al. |
| 8,900,154 B2 | 12/2014 | Stahmann et al. |
| 8,971,936 B2 | 3/2015 | Derchak |
| 8,996,108 B2 | 3/2015 | McCabe et al. |
| 9,028,405 B2 | 5/2015 | Tran |
| 9,107,586 B2 | 8/2015 | Tran |
| 9,192,351 B1 | 11/2015 | Telfort et al. |
| 9,204,796 B2 | 12/2015 | Tran |
| 9,218,454 B2 | 12/2015 | Kiani et al. |
| 9,323,894 B2 | 4/2016 | Kiani |
| 9,326,705 B2 | 5/2016 | Derchak |
| 9,351,640 B2 | 5/2016 | Tran |
| 9,403,018 B2 | 8/2016 | McCabe et al. |
| 9,462,975 B2 | 10/2016 | Sackner et al. |
| 9,492,084 B2 | 11/2016 | Behar et al. |
| 9,526,419 B2 | 12/2016 | Derchak et al. |
| 9,538,980 B2 | 1/2017 | Telfort et al. |
| 9,545,222 B2 | 1/2017 | Derchak et al. |
| 9,622,664 B2 | 4/2017 | An et al. |
| 9,750,429 B1 | 9/2017 | Sackner et al. |
| 9,775,520 B2 | 10/2017 | Tran |
| 9,801,583 B2 | 10/2017 | Derchak et al. |
| 9,814,424 B2 | 11/2017 | Zhang et al. |
| 9,826,903 B2 | 11/2017 | Derchak |
| 9,833,184 B2 | 12/2017 | Derchak et al. |
| 9,901,252 B2 | 2/2018 | Tran |
| 9,907,473 B2 | 3/2018 | Tran |
| 9,955,937 B2 | 5/2018 | Telfort |
| 9,962,092 B1 | 5/2018 | Chawla |
| 10,007,758 B2 | 6/2018 | Al-Ali et al. |
| 10,032,002 B2 | 7/2018 | Kiani et al. |
| 10,045,699 B2 | 8/2018 | Tzvieli et al. |
| 10,055,549 B2 | 8/2018 | Chung et al. |
| 10,064,559 B2 | 9/2018 | Tzvieli et al. |
| 10,080,861 B2 | 9/2018 | Tzvieli et al. |
| 10,092,232 B2 | 10/2018 | Tzvieli et al. |
| 10,113,913 B2 | 10/2018 | Tzvieli et al. |
| 10,130,299 B2 | 11/2018 | Tzvieli et al. |
| 10,130,308 B2 | 11/2018 | Tzvieli et al. |
| 10,136,856 B2 | 11/2018 | Tzvieli et al. |
| 10,255,994 B2 | 4/2019 | Sampath et al. |
| 10,441,181 B1 | 10/2019 | Telfort et al. |
| 2005/0234309 A1 | 10/2005 | Klapper |
| 2006/0020295 A1 | 1/2006 | Brockway et al. |
| 2007/0276278 A1* | 11/2007 | Coyle .................. A61B 5/6805 600/529 |
| 2008/0221468 A1* | 9/2008 | Stahmann ............ A61B 5/0031 600/529 |
| 2008/0275349 A1 | 11/2008 | Halperin et al. |
| 2008/0284587 A1 | 11/2008 | Saigh et al. |
| 2009/0125074 A1 | 5/2009 | Ochs et al. |
| 2010/0063365 A1 | 3/2010 | Pisani et al. |
| 2011/0054289 A1 | 3/2011 | Derchak et al. |
| 2011/0125060 A1 | 5/2011 | Telfort et al. |
| 2011/0213271 A1 | 9/2011 | Telfort et al. |
| 2012/0041279 A1 | 2/2012 | Freeman et al. |
| 2012/0277545 A1 | 11/2012 | Teixeira |
| 2013/0096404 A1* | 4/2013 | Colman ............... A61B 5/0476 600/324 |
| 2013/0226078 A1 | 8/2013 | Zhang et al. |
| 2014/0163425 A1 | 6/2014 | Tran |
| 2014/0303521 A1* | 10/2014 | Nakamura ............. A61B 7/003 600/586 |
| 2014/0304792 A1 | 10/2014 | Derchak et al. |
| 2015/0068069 A1 | 3/2015 | Tran et al. |
| 2015/0126878 A1 | 5/2015 | An et al. |
| 2015/0157273 A1 | 6/2015 | An et al. |
| 2015/0161876 A1 | 6/2015 | Castillo |
| 2015/0190087 A1 | 7/2015 | Shinar et al. |
| 2015/0327810 A1 | 11/2015 | Horii et al. |
| 2015/0342540 A1 | 12/2015 | An et al. |
| 2015/0359467 A1 | 12/2015 | Tran |
| 2016/0004834 A1 | 1/2016 | Criner |
| 2016/0095549 A1 | 4/2016 | Chang |
| 2016/0249826 A1 | 9/2016 | Derchak |
| 2016/0283665 A1 | 9/2016 | Sampath et al. |
| 2016/0314260 A1 | 10/2016 | Kiani |
| 2016/0354032 A1 | 12/2016 | Wariar |
| 2016/0367186 A1 | 12/2016 | Freeman et al. |
| 2017/0028199 A1 | 2/2017 | Roehrlein et al. |
| 2017/0079594 A1 | 3/2017 | Telfort et al. |
| 2017/0157323 A1 | 6/2017 | Saha et al. |
| 2017/0164897 A1 | 6/2017 | Derchak et al. |
| 2017/0209094 A1 | 7/2017 | Derchak et al. |
| 2017/0213368 A1 | 7/2017 | Brayanov et al. |
| 2017/0231505 A1 | 8/2017 | Mahajan et al. |
| 2017/0281095 A1 | 10/2017 | An et al. |
| 2017/0281097 A1 | 10/2017 | Thakur et al. |
| 2017/0290551 A1 | 10/2017 | An et al. |
| 2017/0296052 A1 | 10/2017 | Behar et al. |
| 2017/0296053 A1 | 10/2017 | Thiagarajan |
| 2017/0325779 A1 | 11/2017 | Spina et al. |
| 2017/0347886 A1 | 12/2017 | Tran |
| 2017/0347968 A1 | 12/2017 | Maile et al. |
| 2017/0347969 A1 | 12/2017 | Thakur et al. |
| 2018/0008204 A1 | 1/2018 | An et al. |
| 2018/0043158 A1 | 2/2018 | Thakur et al. |
| 2018/0092588 A1 | 4/2018 | Tzvieli et al. |
| 2018/0098739 A1 | 4/2018 | Freeman et al. |
| 2018/0106897 A1 | 4/2018 | Shouldice et al. |
| 2018/0153416 A1 | 6/2018 | Zile et al. |
| 2018/0153460 A1 | 6/2018 | Ternes et al. |
| 2018/0153477 A1 | 6/2018 | Nagale et al. |
| 2018/0168459 A1 | 6/2018 | Tran |
| 2018/0174680 A1 | 6/2018 | Sampath et al. |

(56) References Cited

U.S. PATENT DOCUMENTS

| | | |
|---|---|---|
| 2018/0184907 A1 | 7/2018 | Tran |
| 2018/0206815 A1 | 7/2018 | Telfort |
| 2018/0280646 A1 | 10/2018 | Freeman et al. |
| 2018/0300919 A1 | 10/2018 | Muhsin et al. |
| 2018/0336970 A1 | 11/2018 | Sherwood et al. |
| 2018/0344200 A1 | 12/2018 | Thakur et al. |
| 2019/0038133 A1 | 2/2019 | Tran |
| 2019/0038180 A1 | 2/2019 | Tzvieli et al. |
| 2019/0046044 A1 | 2/2019 | Tzvieli et al. |
| 2019/0074089 A1 | 3/2019 | Kochura et al. |
| 2019/0082973 A1 | 3/2019 | Knisely |
| 2019/0083789 A1 | 3/2019 | Thakur et al. |
| 2019/0122762 A1 | 4/2019 | Al-Ali et al. |
| 2019/0122763 A1 | 4/2019 | Sampath et al. |
| 2019/0134396 A1 | 5/2019 | Toth et al. |
| 2020/0054238 A1 | 2/2020 | Gopinathan et al. |
| 2020/0261675 A1 | 8/2020 | Rehman et al. |

OTHER PUBLICATIONS

Office Action dated Mar. 30, 2020, for corresponding U.S. Appl. No. 16/547,818, filed Aug. 22, 2019; consisting of 48-pages.
Office Action dated Mar. 20, 2020, for corresponding U.S. Appl. No. 16/548,182, filed Aug. 22, 2019; consisting of 15-pages.
Office Action dated Jan. 29, 2020, for corresponding U.S. Appl. No. 16/548,182, filed Aug. 22, 2019; consisting of 37-pages.
Annex to the Invitation to Pay Additional Fees, dated Dec. 20, 2019, for corresponding International Application No. PCT/US2019/047009, filed on Aug. 19, 2019; consisting of 12-pages.
Final Office Action dated Jul. 1, 2020, for corresponding U.S. Appl. No. 16/548,182, filed Aug. 22, 2019; consisting of 14-pages.
Non-Final Office Action dated Aug. 21, 2020 for corresponding U.S. Appl. No. 16/802,658, filed Feb. 27, 2020; consisting of 39-pages.
Non-Final Office Action dated Feb. 2, 2021, for corresponding U.S. Appl. No. 16/937,691; consisting of 39-pages.
Final Office Action dated Feb. 2, 2021, for corresponding U.S. Appl. No. 16/802,658; consisting of 16-pages.

* cited by examiner

ACOUSTIC SENSOR AND VENTILATION MONITORING SYSTEM

CROSS-REFERENCE TO RELATED APPLICATION

This application is a continuation of U.S. patent application Ser. No. 16/544,033, filed on Aug. 19, 2019, entitled "ACOUSTIC SENSOR AND VENTILATION MONITORING SYSTEM" and is related to and claims priority to U.S. Provisional Patent Application Ser. No. 62/857963, filed Jun. 6, 2019 entitled "ACOUSTIC SENSOR AND VENTILATION MONITORING SYSTEM", and is also related to and claims priority to U.S. Provisional Patent Application Ser. No. 62/719918, filed on Aug. 20, 2018 entitled "ACOUSTIC SENSOR SYSTEM", the entirety of which is incorporated herein by reference.

TECHNICAL FIELD

This disclosure relates to a method and system for a non-invasive real-time monitoring system with diagnostic algorithms that continuously quantify and analyze the pattern of an ambulatory person's respiratory rate (RR), tidal volume (TV), degree of upper airway obstruction (talking/snoring), body activity level, body coordination, body position, heart rate, and/or temperature, among other physiological conditions.

BACKGROUND

Respiratory rate (RR) is routinely monitored during research studies using a tight-fitting band around the wearer's chest or impedance pneumography. In impedance pneumography, a bedside monitor measures/analyzes the change in electrical impedance across the patient's thorax during inhalation/exhalation to measure RR accurately. Current respiratory monitors for in-hospital use measure a change in thoracic electrical impedance to measure minute ventilation (RR×Tidal Volume (TV)). An array of wearable electrodes is hard-wired to an expensive bedside monitor/display with threshold and predictive alarms for hypoventilation.

Clinicians commonly use a modified nasal oxygen cannula and capnography in a hospital's ER, OR, ICU, and general floors to continuously monitor respiratory rate and the exhaled carbon dioxide concentration. The nasal cannulas are cumbersome and easily dislodged from the nose leading to a high degree of false alarms. Hospitals also commonly use a pulse oximeter to continuously monitor a patient's hemoglobin oxygen saturation. Unfortunately, a pulse oximeter alarms for arterial hypoxemia only after moderate to severe hypoventilation, especially if the hospitalized patient is being managed with supplemental oxygen therapy.

Breathing abnormalities, such as hypoventilation commonly occur as a side effect of central nervous system depressant drugs, for example, opioids, benzodiazepines, barbiturates, etc., with and without alcohol ingestion. The human body's ten trillion cells continuously produce carbon dioxide as a waste product of aerobic metabolism. Carbon dioxide molecules are continuously transported in the flowing blood to the lung's alveoli for excretion into the external environment. The human body has a variety of physiological mechanisms for maintaining the partial pressure of carbon dioxide in arterial blood within a precise range ($PaCO_2$ 40 mm Hg +/−5 mm Hg) by increasing and decreasing the amount of air that moves into and out of the lung's alveoli.

Hypoventilation is defined as an abnormally elevated level of carbon dioxide in the arterial blood ($PaCO_2 > 45$ mm Hg or respiratory acidosis). This occurs when the amount of alveolar ventilation does not satisfactorily excrete the amount of $CO_2$ produced by the cells- leading to an elevated concentration of $CO_2$ in the arterial bloodstream. Although the impact caused by hypoventilation is well-recognized, quantitative measurement of ventilation, whether increased or decreased ventilation, has not been well established in clinical diagnostics. For example, a nurse on the general ward of a hospital is required to observe a patient's breathing for a full minute, while counting the number of breaths and estimating the depth of breathing. This nursing assessment occurs infrequently and is prone to error. This is in part due to the inability to continuously and accurately monitor/measure airflow into and out of the lungs during ambulation in the hospital or real-world environment. The amount of air that moves into and out of the trachea, bronchi, and alveoli per minute is called minute ventilation. The amount of air that moves into and out of the alveoli per minute is called alveolar minute ventilation. The amount of air that moves into and out of the trachea and bronchi, but does not move into/out of the alveoli is called dead space ventilation. The body uses chemoreceptors to continuously measure the arterial blood's pH level and $CO_2$ concentration. An elevated carbon dioxide concentration (respiratory acidosis) stimulates the brain to increase alveolar minute ventilation by increasing the RR and/or TV. A decreased carbon dioxide concentration (respiratory alkalosis) stimulates the brain to decrease minute ventilation by decreasing the RR and/or TV. Hypoventilation occurs when the alveolar minute ventilation does not excrete the amount of carbon dioxide currently produced by cellular metabolism. Hyperventilation occurs when the alveolar minute ventilation exceeds the amount of carbon dioxide currently produced by cellular metabolism. Thus, known methods of measuring respiratory rate by airflow such as nasal cannula capnography and temperature thermistors are used by clinicians to diagnose disordered breathing during a sleep apnea study, as opposed to being awake and ambulatory. Capnography continuously samples air from one nostril using a nasal cannula, and displays a $CO_2$ concentration waveform during inhalation/exhalation. The temperature thermistor measures changes in air temperature within one nostril during inhalation/exhalation (exhaled air warmer), These semi-quantitative measures of respiration are used to detect apneas and hypopneas by correlating relative changes in airflow, but are not suited to quantify the degree of upper airway function or level of ventilation impairment.

SUMMARY

The techniques of this disclosure generally relate to a method, device, and system for an acoustic ventilation monitoring system.

In one aspect, a method of monitoring respiration with an acoustic measurement device, the acoustic measurement device having a sound transducer, the sound transducer configured to measure sound associated with airflow through a mammalian trachea includes correlating the measured sound into a measurement of tidal volume and generating at least one from the group consisting of an alert and an alarm if the measured tidal volume falls outside of a predetermined range.

In another aspect, the measurement of sound associated with airflow through the trachea occurs at least periodically.

In another aspect, the acoustic measurement device includes a housing, and wherein the sound transducer is suspended within the housing.

In another aspect, the housing of the acoustic measurement device has a width between 0.5 cm and 2.5 cm.

In another aspect, the housing defines an opening, and wherein the sound transducer is disposed on an end of the housing opposite the opening.

In another aspect the housing is configured to releasably couple to skin of the mammalian trachea.

In another aspect the housing includes a diaphragm configured to vibrate in response to sound.

In another aspect the housing is configured to engage coupling component releasably adhered to the skin, and wherein the coupling component includes the diaphragm.

In another aspect the housing includes a connector configured to engage the coupling component.

In another aspect, the acoustic measurement device further includes an accelerometer configured to measure a relative body position and a movement of the mammal, and wherein the method further includes modifying the respective predetermined range on the mammal's relative position and movement.

In another aspect, the acoustic measurement device further includes at least one from the group consisting of a device configured to measure a patient's cardiac electrogram, temperature, and blood oxygenation.

In another aspect, the method includes calculating at least one from the group consisting of a rate of change and trend direction of the measured tidal volume, and wherein the at least one from the group consisting of the alert and the alarm is further generated if the calculated rate of change and trend direction of the tidal volume falls outside the predetermined range.

In another aspect, the method includes filtering out ambient noise from the measured sound.

In one aspect, an acoustic measurement device includes a housing defining a chamber therein, the housing defining a width and a length of 2 cm or less, the housing defining an opening. A sound transducer is disposed within the chamber opposite the opening; an adhesive surrounding the opening. A wireless transmitter is in communication with the sound transducer.

In another aspect, the housing is surrounded by a sound insulation material except around the opening.

In another aspect, the device includes a diaphragm disposed within the opening and coextensive with a surface of the housing, the diaphragm being configured to resonate in response to sound.

In another aspect, the diaphragm is coupled to the sound transducer.

In another aspect, the device includes a power source coupled to the housing, wherein the power source is configured to power the wireless transmitter.

In another aspect, the housing includes a first connector configured to engage a second connector of a coupling component, the coupling component being configured to be adhered to the patient's skin, and wherein the coupling component includes an adhesive and a diaphragm, the adhesive being disposed about at least a portion of the second connector and the diaphragm.

In one aspect, an acoustic ventilation monitoring system includes an acoustic measurement device, the acoustic measurement device includes a housing defining a chamber therein, the housing defining a width and a length of 2 cm or less, the housing defining an opening and being configured to releasably couple to a surface proximate a patient's trachea. A sound transducer is disposed within the chamber opposite the opening configured to measure sound energy emanating from the patient's trachea and lungs. A wireless transmitter is in communication with the sound transducer. A controller is in communication with the acoustic measurement device, the controller being configured to: correlate the measured sound energy into a measurement of the patient's tidal volume and respiratory rate in real-time, assign a first value of a likelihood of an adverse event based on the measured respiratory rate, assign a second value of a likelihood of the adverse event based on the measured tidal volume, calculate a rate of change of the measured respiratory rate and tidal volume over time, assign a third value of a likelihood of the adverse event based on the calculated rate of change of the measured respiratory rate, assign a fourth value of a likelihood of the adverse event based on the calculated rate of change of the measured tidal volume, multiply the third value and the fourth value by a predetermined weighing factor, and generate an alert if a sum of the first value, the second value, the third value, and the fourth value, exceeds a predetermined risk score threshold.

In one aspect, a method of predicting an opioid overdose with an acoustic measurement device, the acoustic measurement device having a sound transducer, the sound transducer configured to measure sound associated with airflow through a mammalian trachea includes correlating the measured sound into a measurement of tidal volume and generating at least one from the group consisting of an alert and an alarm if the measured tidal volume falls outside of a predetermined range, the at least one of the alert and the alarm indicating a likelihood of an opioid overdose.

In another aspect, the measurement of sound associated with airflow through the trachea occurs at least periodically.

In another aspect, the acoustic measurement device includes a housing, and wherein the sound transducer is suspended within the housing.

In another aspect, the housing of the acoustic measurement device has a width between 0.5 cm and 2.5 cm.

In another aspect, the housing defines an opening, and wherein the sound transducer is disposed on an end of the housing opposite the opening.

In another aspect, the housing is configured to releasably couple to skin of the mammalian trachea.

In another aspect, the housing includes a diaphragm configured to vibrate in response to sound.

In another aspect, the housing is configured to engage coupling component releasably adhered to the skin, and wherein the coupling component includes the diaphragm.

In another aspect, the housing includes a connector configured to engage the coupling component.

In another aspect, the acoustic measurement device further includes an accelerometer configured to measure a relative body position and a movement of the mammal, and wherein the method further includes modifying the respective predetermined range on the mammal's relative position and movement.

In another aspect, the method further includes calculating at least one from the group consisting of a rate of change and trend direction of the measured tidal volume, and wherein the at least one from the group consisting of the alert and the alarm is further generated if the calculated rate of change and trend direction of the tidal volume falls outside the predetermined range.

In another aspect, the method further includes filtering out ambient noise from the measured sound.

In one aspect, a method of predicting an opioid overdose in a mammal includes continually measuring sound waves emanating from an airflow into and out of the mammalian trachea with an acoustic measurement device releasably affixable to the mammal's skin proximate the trachea. The measured sound is correlated into a measurement of the mammal's respiratory rate and tidal volume. A direction trend and rate of change of the respiratory rate and tidal volume at a predetermined interval are calculated. During the predetermined interval, a value is assigned to the mammal's (a) respiratory rate and tidal volume; (b) direction trend of the respiratory rate and tidal volume; and (c) rate of change of the respiratory rate and tidal volume. (a), (b), and (c) are summed. At least one from the group consisting of an alert and an alarm is generated if the sum of (a), (b), and (c) falls outside of a predetermined opioid risk range.

In another aspect, the method includes multiplying the assigned value of at least one from the group consisting of (b) and (c) by a predetermined weighting value.

In another aspect, the acoustic measurement device further includes an accelerometer, and where the method further includes continually measuring a mammal's activity level, body position, and snoring level; calculating a direction trend and rate of change of the measured activity level, body position, and snoring level at the predetermined interval. During the predetermined interval, a value is assigned to the mammal's: (d) activity level, body position, and snoring level; (e) direction trend of the activity level, body position, and snoring level; and (f) rate of change of the activity level, body position, and snoring level. (a)-(f) is summed. The at least one from the group consisting of the alert and the alarm is generated if the sum of the (a)-(f) falls outside of the predetermined opioid risk range.

In another aspect, the method includes adhering an acoustic measuring device to the skin of the mammal proximate the trachea.

In another aspect, the acoustic measuring device is configured to be in communication with a remote controller, the remote controller being configured to carry out the recited method steps.

In another aspect, the method includes multiplying the assigned value of at least one from the group consisting of (d), (e), and (f) by the predetermined weighting value.

In another aspect, the acoustic measurement device is wireless.

In one aspect, a method of predicting an opioid overdose includes at least periodically measuring sound energy emanating from an airflow into and out of the mammal's trachea and lungs with an acoustic measurement device, the acoustic measurement device including a housing including at least two sound transducers, the housing being sized and configured to be adhered to a mammal's trachea with a coupling component, the housing defining an opening, the at least two sound transducers being disposed within the housing opposite the opening. The measured sound is wireless communicated to a remote controller, the remote controller being configured to: correlate the measured sound energy into a measurement of the mammal's respiratory rate and tidal volume; assign a first value of a likelihood of the opioid overdose based on the measured respiratory rate; assign a second value of a likelihood of the opioid overdose based on the measured tidal volume; calculate a rate of change of the measured respiratory rate and tidal volume at over the predetermined interval; assign a third value of a likelihood of the opioid overdose based on the calculated rate of change of the measured respiratory rate; assign a fourth value of a likelihood of the opioid overdose on the calculated rate of change of tidal volume and generate at least one from the group consisting of an alert and alarm if the sum of the first value, the second risk, the third value, and the fourth value, exceed the predetermined risk score threshold.

In one aspect, a method of predicting heat exhaustion or heat stroke in an ambulatory mammal includes at least periodically measuring sound emanating from an airflow through the mammal's trachea with an acoustic measurement device, the acoustic measurement device including a housing including a sound transducer and a temperature sensor. The measured sound is correlated into a measurement of the mammal's respiratory rate and tidal volume. A first value of a likelihood of at least one of heat exhaustion and heat stroke is assigned to the measured respiratory rate and a second value is assigned to the measured tidal volume. The mammal's temperature is measured at least periodically. A third value of a likelihood of at least one of heat exhaustion and heat stroke is assigned to the measured temperature. At least one from the group consisting of an alert and an alarm is generated if a comparison between the first value, second value, and third value exceeds a predetermined range.

In another aspect, the method includes multiplying at least one from the group consisting of the first value, the second value, and the third value by a predetermined weighting value.

In another aspect, the housing of the acoustic measurement device has a width between 0.5 cm and 2.5 cm.

In another aspect, the housing defines an opening, and wherein positioning the acoustic measurement device on the skin of the mammal includes pressing the opening of the housing against the mammal's skin.

In another aspect, the sound transducer is disposed on an end of the housing opposite the opening.

In another aspect, the housing includes a diaphragm configured to vibrate in response to sound disposed within the opening and pressed against the mammal's skin.

In another aspect, the diaphragm is directly coupled to the sound transducer.

In another aspect, the acoustic measurement device further includes an accelerometer configured to measure a relative body position and a movement of the mammal, and wherein the method further includes at least periodically modifying the predetermined range based on the mammal's relative position and movement.

In another aspect, the acoustic measurement device further includes at least one from the group consisting of a device configured to measure a mammal's cardiac electrogram and blood oxygenation.

In another aspect, the method includes calculating at least one from the group consisting of a rate of change and trend direction of the sum of the first value and the second value, and wherein the at least one from the group consisting of the alert and the alarm is further generated if the calculated rate of change and trend direction of the sum of the first value and the second value deviates from the predetermined range.

In another aspect, the housing includes a first connector configured to engage a second connector of a coupling component, the coupling component being configured to be adhered to the mammal's skin, and wherein the coupling component includes an adhesive and a diaphragm, the adhesive being disposed about at least a portion of the second connector and the diaphragm.

In one aspect, a method of tracking fitness of an ambulatory mammal includes at least periodically measuring sound emanating from airflow through an ambulatory mammal's trachea during exercise with an acoustic measurement device releasably affixable to the mammal's skin proximate the trachea, the acoustic measurement device including a housing including a sound transducer. The measured sound is correlated into a measurement of the mammal's respiratory rate and tidal volume. The mammal's minute respiratory volume (MV) is calculated. The mammal's MV is compared with a predetermined MV threshold. The ambulatory mammal's fitness is based on the comparison.

In one aspect, the housing of the acoustic measurement device has a width between 0.5 cm and 2.5 cm.

In one aspect, the housing defines an opening, and wherein positioning the acoustic measurement device on the skin of the mammal includes pressing the opening of the housing against the mammal's skin.

In one aspect, the sound transducer is disposed on an end of the housing opposite the opening.

In one aspect, the housing includes a diaphragm configured to vibrate in response to sound disposed within the opening and pressed against the mammal's skin.

In one aspect, the diaphragm is directly coupled to the sound transducer.

In one aspect, the acoustic measurement device further includes an accelerometer configured to measure a relative body position and a movement of the mammal, and wherein the method further includes continuously modifying the respective predetermined threshold based on the mammal's relative position and movement.

In one aspect, the acoustic measurement device further includes at least one from the group consisting of a device configured to measure a mammal's cardiac electrogram and blood oxygenation.

In one aspect, the housing includes a first connector configured to engage a second connector of a coupling component, the coupling component being configured to be adhered to the mammal's skin, and wherein the coupling component includes an adhesive and a diaphragm, the adhesive being disposed about at least a portion of the second connector and the diaphragm.

An Acoustic Ventilation Monitoring System (AVMS) is configured to measure and analyze a pattern of variables such as respiratory rate (RR), tidal volume (TV), upper airway patency (talking, snoring, apnea), body activity, body coordination, body position, heart rate, and temperature in ambulatory and hospitalized patients. All of these variables may be analyzed in real-time to update a Risk-Index Score (RIS) that calculates the current and future risk of an adverse clinical event.

The AVMS determines whether an amount and pattern of minute ventilation (MV) and other variables are stable and within normal limits, or unstable and above or below the normal range. The diagnostic algorithms may produce alerts and alarms when they detect an unstable pattern of MV or the onset of mild, moderate, and severe hypoventilation or hyperventilation; based upon a change from an individual patient's baseline; or a change from a population baseline based upon height, weight, age, and sex.

In one configuration, the AVMS includes a wearable Trachea Sound Device (TSD) that transmits data to a diagnostic software application on the patient's cell phone that alerts/alarms when it detects/predicts a significant change in physiology that increases the immediate risk for a serious adverse event. The TSD continuously measures the sound of air moving into and out of the trachea during inhalation. In one configuration, the TSD includes two microphones, an accelerometer, circuitry, flash memory, a telemetry chip, software, and a rechargeable battery housed within a miniature stethoscope head. In other configurations, additional sensors and diagnostic algorithms that quantify and analyze the ambulatory patient's electrocardiogram, hemoglobin oxygen saturation, and pulse oximeter waveform are included. In another configuration, the wearable TSD uses the electrocardiogram signal and the pulse oximeter waveform signal to calculate the ambulatory patient's blood pressure (BP) using pulse transmit time. The TSD continuously communicates with a software application on the patient's cell phone via low power Wi-Fi, Bluetooth, or other RFID communications.

The AVMS continuously monitors the respiratory function of the patient using real-time diagnostic algorithms based upon physiological modeling, pharmacologic modeling, machine learning, deep learning, and artificial intelligence methods. In one configuration, the user's smartphone transmits key data to a central monitoring station for advanced analysis by a computer and clinician. Algorithms of the AVMS analyze the ambulatory patient's amount and pattern of MV using the real-time RR and TV measurements produced by the TSD. The AVMS alerts/alarms to notify the patient when the amount and pattern of MV is lower than normal (hypoventilation), higher than normal (hyperventilation), and/or an unstable pattern of MV. The AVMS continuously monitors MV and other physiological markers to determine stability of the patient's cardiovascular, pulmonary and metabolic systems during daily activities. The amount of alveolar minute ventilation directly correlates with the amount of cellular metabolism during normal lung function.

In one configuration, the AVMS continuously measures, analyzes, records, and displays the RR, TV, MV, airway patency, HR, body temperature, body activity level, body coordination, and body position of an ambulatory patient in the real-world environment; and a patient admitted to the hospital. Hospital clinicians may use the AVMS's real-time MV, HR, body activity, and temperature trend data to manage inpatient medical therapy in a more efficient/effective/timely manner- leading to improved clinical outcomes and decreased costs.

The AVMS continuously monitors an ambulatory mammal's respiratory health in their real-world environment during daily activities. In one configuration, the system automatically alerts, for example, the patient, family members, and caregivers by text, e-mail, and phone call when detecting or predicting an increased risk for a serious adverse clinical event. One embodiment automatically calls 911 emergency personnel with patient location and vital sign information. Another embodiment combines the AVMS with a wearable or implantable drug infusion pump with a closed-loop control algorithm. For example, outpatients and hospitalized patients taking opioid medication for acute or chronic pain may wear the AVMS in communication with a patch pump capable of automatically infusing a bolus and/or infusion of the opioid reversal medication Naloxone (Narcan). The wearable TSD measures and processes the vital sign signals to enhance the signal-to-noise ratio. Data from the TSD is transmitted to the patient's cell phone (or other smart device) for automated analysis by diagnostic algorithms. The smart device's algorithms continuously calculate a Risk-Index Score (RIS) for a variety of acute and chronic medical conditions to determine when to alert and alarm. Data may be transmitted from the patient's smart device to a central monitoring station's electronic medical record for advanced analysis by a controller/computer and clinician. The controller may automatically summarize the data from the TSD and interpret the clinically significance in a brief written report to the patient, patient's physician's, patient's hospitals, and and/or a patient's central electronic medical record (EMR). Each patient has a detailed medical/ surgical history and medication list stored in the central monitoring station. The patient and caregivers may receive real-time alerts and alarms by text, e-mail, or phone call. Hospitals and physicians can request summarized patient data from the central monitoring station's electronic medical record under HIPA guidelines. In another configuration, the AVMS functions as a fitness monitor that continuously measures, records, and displays the ambulatory person's respiratory rate, tidal volume (minute ventilation), heart rate, temperature, body position, and body activity level.

Clinicians interpret recorded and real-time AVMS data to diagnose clinical deterioration and adjust outpatient medical therapy in a more efficient/effective/timely manner—leading to improved clinical outcomes and decreased costs. Outpatients with congestive heart failure (CHF), ischemic heart disease, chronic obstructive pulmonary disease (COPD), asthma, pneumonia, cystic fibrosis, pneumoconiosis, muscular dystrophies, pulmonary embolism, and other cardiovascular and pulmonary diseases develop an unstable pattern of MV, HR, activity level, and temperature during an episode of clinical deterioration. Patients commonly experience an increase in the work-of-breathing (MV) that presents as shortness-of breath or dyspnea during daily activities. A prolonged period of hard breathing causes fatigue. For example, outpatients with worsening congestive heart failure (CHF) have an increase in the work-of-breathing (MV) due to an increase in pulmonary edema (lung water), a decrease in lung compliance, and a low blood oxygen concentration. The heart rate and body temperature also increase due to an increase in cellular metabolism, cardiac work, and hypoxemia. An increase in the work-of-breathing is commonly described by the patient as an increase in shortness-of-breath during daily activities. A prolonged period of increased work-of-breathing causes the patient to experience the signs and symptoms of fatigue.

An outpatient with respiratory insufficiency/failure due to worsening bronchitis, emphysema, asthma, pneumonia, etc. develops an increase in the work-of-breathing (MV) in response to a decrease in the blood oxygen concentration (hypoxemia), an increase in the blood carbon dioxide concentration (hypercarbia), and/or a decrease in lung volumes. Worsening lung function is caused by airway narrowing, airway obstruction, increased lung water, infection, secretions, and skeletal muscle weakness and fatigue. Decompensation may cause an increase in the RR, TV, MV, HR, body temperature, prolonged exhalation time, and increase the amount of coughing, wheezing, sneezing, yawning, swallowing, and clearance of airway secretions.

The AVMS continuously monitors the MV of a patient taking opioids and/or other medications that cause respiratory depression (for example: morphine, codeine, fentanyl, carfentanil, midazolam, propofol, opium, heroin, methadone, valium, alcohol, and sleeping pills, (Ambien®, Dalmane®, Halcion®, Lunesta® , Prosom®, Restoril®, Rozerem®, Silenor®, Sonata®, Desyrel®, and Belsomra®). This AVMS has diagnostic algorithms optimized to detect/predict the onset and progression of mild to moderate to severe hypoventilation due to opioids and other medications that cause respiratory depression prior to a severe hypoventilation event, as discussed in more detail below.

The AVMS may continuously measure and analyze the MV of hospitalized patients during monitored anesthesia care (MAC) anesthesia with spontaneous ventilation (for example during: regional anesthesia, GI endoscopy, cardiac catheterization, and radiology procedures). Anesthesiologists may use the AVMS to continuously monitor the patient's MV and airway patency in the operative room (OR), Post-Anesthesia Care Unit (PACU), and the Intensive Care Unit (ICU). Hospital clinicians may use the system to continuously monitor the patient's MV and airway patency during sedation procedures in the emergency room, radiology suite, and cardiac catheterization laboratory. Floor nurses may use the AVMS to continuously monitor the patient's MV when managed with opioids and other medications that cause respiratory depression. In one embodiment, medical and surgical patients in the hospital may be continuously monitored using the AVMS with real-time alerts and alarms. The MV trend data is displayed at the bedside and nursing station, and automatically uploaded into the hospital's EMR.

Patients taking opioids and/or other medications that cause respiratory depression at hospital discharge may continue to be monitored at home using the AVMS, with data transmitted to a software application on the patient's cell phone. For example, elderly patients undergoing a hip or knee replacement orthopedic surgery are routinely discharged from the hospital 24 to 48 hours post-operatively—with a prescription for 5 to 7 days of an oral opioid medication for acute pain control. Hospitals, physicians, and nurses may use the AVMS after hospital discharge to enhance patient safety, improve clinical outcome, and minimize the risk of a malpractice lawsuit. Clinicians can download the recorded data to evaluate patient safety and adherence/compliance to the treatment plan. The AVMS can be used in a similar way to enhance the safety and compliance of patients with an opioid-use disorder being treated in an inpatient/outpatient drug rehabilitation (methadone) clinic.

Humans develop a typical pattern of respiratory depression following a large dose of an opioid (alone or mixed with alcohol or sedatives) characterized as a progressive decrease in RR, a decrease in TV, a decrease in talking, an increase in snoring, a decrease in body activity, a progression from coordinated to uncoordinated movements, a change from the upright to the lateral/supine/prone position, an unstable heart rate, and/or an unstable body temperature. The microphones and accelerometer qualify the amount and pattern of head bobbing, snoring, body activity level, body coordination, and body position in real-time to determine the degree of sedation. Sensor data may be transmitted via the patient's smart device (smart phone, smart watch, tablet PC, Alexa, cable box) to a central monitoring station's electronic medical record for advanced analysis by a computer and clinician. A brief summary of an important event may be transmitted electronically to the patient, the patient's physicians, and the patient's hospitals for download into their electronic medical record (EMR).

Patients with an opioid abuse disorder may be treated in an outpatient/inpatient drug and alcohol rehabilitation clinic with the AVMS to prevent brain damage and death due an opioid overdose. Progressive alerts and alarms may be sent to the patient's cell phone, caregivers' cell phones, and/or emergency personnel (911 with location). Clinicians may prescribe the real-time AVMS for safety from hypoventilation and compliance prior to prescribing the next dose of methadone. Sensor data may be downloaded during each clinic visit to evaluate the patient's RIS for hypoventilation since the last visit. In one configuration, patients are required to continuously use the AVMS in order to obtain their next dose of methadone. Recent guidelines from the Hospital Joint Commission and the Center for Medicare and Medicaid calls for all hospitalized patients being managed with opioid medication to be continuously monitored with alarms. Hospital nurses currently monitor patients managed with opioids by assessing the adequacy of ventilation intermittently by observing the depth of breathing and by measuring the number of breaths/minute. Hospitalized patients may be continuously monitored using a hard-wired pulse oximeter, capnometer, or electrical impedance monitor.

In another configuration, the AVMS automatically triggers an auto-injector device (not shown) to deliver an opioid reversal medication (for example naloxone) into the subcutaneous tissue (saving lives). This AVMS may continuously monitor the ventilation status of an ambulatory patient taking opioids in real-time and automatically delivers an opioid antidote when the device detects/predicts high risk for an opioid overdose. The auto-injector may deliver one or more boluses of naloxone or continuously infuse naloxone into the subcutaneous tissue based upon the real-time AVMS data using a closed-loop control algorithm. In another configuration, amateur athletes, professional athletes and the military may use the AVMS to monitor their fitness during exercise and to optimize physical fitness. Performance training is evaluated and optimized using objective measurements of MV, heart rate (HR), and body temperature in relation to the level and duration of exercise. Athletes and soldiers adapt their training program to enhance stamina and endurance using the objective measurements of RR, TV, MV, HR, and temperature. The military and professional versions of the wearable AVMS fitness monitor detect/predict the onset of overheating/exhaustion with alerts and alarms prior to an adverse clinical event.

In another configuration, the AVMS also monitors the ambulatory person's electrocardiogram, percent hemoglobin oxygen saturation, and the pulse oximeter waveform. The electrocardiogram monitors the ambulatory patient's heart rate, heart rhythm and ST segment depression/elevation in relation to the work-of-breathing, HR, and level of activity. The reflectance pulse oximeter monitors the heart rate, hemoglobin oxygen saturation, pulse waveform, and an estimate of the systolic/mean/diastolic blood pressure (using pulse transit time measurement and analysis of the photoplethysmograph waveform). The system can automatically turn the pulse oximeter and electrocardiogram on/off at a set schedule to save battery power; or turn them on only when the algorithms detects or predicts a significant change in the RIS.

In one configuration, the TSD is adhered to the skin surface adjacent to the larynx and/or proximal trachea. Microphones measure the sound of air moving with the trachea lumen during inhalation and exhalation. The AVMS analyzes the sound information to accurately estimate respiratory rate (RR), tidal volume (TV), number and duration of apnea episodes, and degree of upper airway obstruction (snoring). Real-time TSD data may be recorded, downloaded, analyzed, and displayed on any smart device with wireless communication. Data may be transferred to a central monitoring station for advanced analysis by a computer and clinician. The device may alert and alarm when the algorithms detects a significant change in physiology, based upon a real-time RIS. The risk-index algorithm's ability to detect/predict at which point during treatment with an opioid does mild, moderate, and severe hypoventilation actually occur. The degree of hypoventilation during hospital care and research studies may be based upon the concentration of carbon dioxide in artery blood (PaCO2). For example, the algorithm is contoured to detect mild hypoventilation (PaCO2—45 to 50 mm Hg) due to an opioid overdose with high sensitivity (>90%) and specificity (>90%), moderate hypoventilation (PaCO2—51 to 60 mm Hg) due to an opioid overdose with high sensitivity (>95%) and specificity (>95%), and severe hypoventilation (PaCO2>60 mm Hg) due to an opioid overdose with high sensitivity (>99%) and specificity (>99%). The algorithms use a RIS to accurately detect and predict the onset of mild, moderate, and severe hypoventilation prior a severe hypoventilation event due to a medication overdose (opioids, alcohol, benzodiazepam, etc.) or other medical conditions.

In this configuration, the AVMS includes a wearable TSD that continuously measures the volume of air flowing through the patient's mid-trachea during each inhalation and exhalation (ml/kg/minute). The TSD uses microphone sound data and 3-axis accelerometer data to accurately measure respiratory rate (RR), tidal volume (TV), minute ventilation (MV), the timing of inhalation/exhalation, degree of upper airway obstruction (talking, snoring, apnea), body activity level, body coordination, and body position. A typical tidal volume (TV) at rest is approximately 500 ml/breath (amount of air moved into the body during inspiration and out of the body during exhalation). Thus, a typical adult person at rest may have a minute ventilation of approximately 6000 ml/minute (12 breaths/min×500 ml tidal volume/breath =6 L/min). The normal minute ventilation during a period of rest ranges from 5 to 8 L/minute in adult humans. Minute ventilation during light activities may increase to 12 L/minute, and may increase to >40 L/minute during moderate exercise.

The real-time algorithms may analyze the amount and pattern of the ambulatory patient's breathing (RR×TV=MV) to determine the "Work of Breathing" in relation to the level of body activity. The algorithms may accurately quantify the degree of hypoventilation, hyperventilation, hypopnea, hyperpnea, tachypnea, bradypnea, apnea and other abnormal patterns of ventilation.

Hypoventilation is defined as an elevated partial pressure of carbon dioxide in the blood (PaCO2>45 mm Hg) due to insufficient minute ventilation relative to the metabolic production of CO2. Hyperventilation is defined as a decreased partial pressure of carbon dioxide in the blood (PaCO2<35 mm Hg) due to excessive minute ventilation relative to the metabolic production of CO2. Hypopnea is defined as overly shallow breathing or an abnormally low respiratory rate. Hyperpnea is defined as an increased depth and rate of breathing. Bradypnea is defined as abnormally slow respiratory rate. Tachypnea is defined as abnormally fast respiratory rate. Apnea is defined as a pause in breathing, where there is no movement of the muscles of inhalation or chest wall (for example >15 seconds), and the volume of the lungs_remains unchanged.

The TSD may also monitor upper airway patency/degree of airway obstruction (normal sound patterns, talking, snoring), body activity, body position, and body coordination to determine the sleep/awake cycle and estimate of the level of sedation. The TSD may also monitor the amount and pattern of coughing, sneezing, wheezing, yawning, swallowing, and clearance of airway secretions.

In one configuration, the wearable TSD includes telemetry to a cell phone application and is approximately a dime-sized sensor (for example 1.0 cm diameter×0.675 cm height) that reliably transmits trachea sound and accelerometer data to an adjacent cell phone. The miniature sensor is easily attached to/detached from the disposable ring and adhesive base (for example 2.0 cm diameter×0.2 cm height) with a twist and click motion. This disposable base can be adhered to the skin over the trachea immediately above the sternal notch or lateral to the larynx for up to 14 days, while the sensor can be easily attached/detached from the base as needed for recharging the battery. In addition, the tracheal sounds can be signal processed and analyzed using frequency versus time curves and amplitude versus time curves to diagnose a normal pattern of inhalation and a normal pattern of exhalation (clear uninterrupted sound pattern) in contrast to abnormal inhalation/exhalation sounds. Sleep apnea and other pathological conditions commonly cause intermittent upper airway obstruction that can lead to hypoventilation, hypoxemia, arrhythmias, pulmonary hypertension, and heart failure. Opioids, alcohol, illegal drugs, and other medications that cause sedation may cause relaxation of the upper airway muscles, leading to mild to moderate to severe upper airway obstruction (snoring and obstructive apnea). Analysis of the partially obstructed upper airway sound patterns can be used to diagnosis the progression of airway muscle relaxation as an estimate of the severity of sleep apnea or the degree of central nervous system sedation.

The wearable TSD incorporates microphones and an accelerometer on a motherboard containing electronics, flash memory, a telemetry chip, and a rechargeable battery. The wearable TSD may incorporate an additional microphone (on the TSD or the cell phone) as an input for ambient noise cancellation and noise suppression. The wearable TSD is mechanically adhered to the skin over the proximal trachea (in the midline just above the sternal notch or adjacent to the larynx) by a small plastic base with an adhesive pad and maybe include coloring to match the skin tone of the patient to increase acceptance of the wearable TSD. The base may mechanically couple a flexible diaphragm to the skin over the proximal trachea. The wearable TSD can be easily attached/detached from the adhesive base with a twist and click motion. The sensor base can stay adhered to the skin for up to 2 weeks, while the wearable TSD can be changed out every few days for recharging the battery. The TSD's microphones may be positioned at the focal point above the diaphragm to accurately measure the sound of air movement within the trachea during inhalation/exhalation.

The monitoring system may have progressive alerts and alarms to the patient's cell phone, a caregiver, and/or 911 emergency personnel (with location). The wearable TSD can also transmit data to a bedside hospital monitor or a nurse's smart device for analysis and display. The AVMS further has the capability of predicting the onset of opioid induced respiratory depression (hypoventilation) using a real-time RIS updated, for example, every 20 to 30 seconds.

Physicians and nurses that manage outpatients with chronic pain can use the AVMS as an objective way to enhance clinical safety, patient education, and compliance with taking their prescribed pain medication. Sensor data may be downloaded during each clinic visit to evaluate the patient's RIS for hypoventilation. Physicians and physician assistants may prescribe short-term use of the wearable TSD following initiation of opioid therapy, and an escalation in opioid dose. Humans developing an opioid overdose typically develop a progressive decrease in RR, a decrease in TV, progression from normal ambulation to uncoordinated movements, decreased talking, increased snoring, decreased body activity, and a change from the upright to lateral/supine/prone positions.

In addition, a wide variety of pathological conditions can cause hypoventilation, for example, severe obesity (obesity-hypoventilation syndrome), neuromuscular disorders (e.g., amyotrophic lateral sclerosis, muscular dystrophies with diaphragm paralysis, Guillain-Barré syndrome, myasthenia gravis, etc.), chest wall deformities, obstructive sleep apnea, chronic obstructive lung disease, ischemic brain injury, neurologic disorders (e.g., encephalitis with brainstem disease, trauma, poliomyelitis, multiple sclerosis, etc.),central alveolar hypoventilation, and sudden infant death syndrome among other disorders and diseases.

Some embodiments advantageously provide a method and system for monitoring a patient's breathing, the method including positioning an acoustic measurement device on the skin of a patient proximate one of the trachea and/or a lateral neck region of the patient. The acoustic measurement device may include a housing defining a chamber and a sound transducer suspended within the chamber. The method further includes measuring at least one from a group consisting of a respiratory rate and a tidal volume with the acoustic measurement device. The measurement of the at least one from the group consisting of the respiratory rate and the tidal volume is transmitted to a remote controller. The remote controller is configured to compare the measurement of the at least one from the group consisting of respiratory rate and tidal volume to a respective one of a fixed or a dynamic threshold and determine an adverse event in real time if the measurement of the at least one from the group consisting of respiratory rate and tidal volume deviates from the respective predetermined threshold by a predetermined amount.

BRIEF DESCRIPTION OF THE DRAWINGS

A more complete understanding of embodiments described herein, and the attendant advantages and features thereof, may be more readily understood by reference to the following detailed description when considered in conjunction with the accompanying drawings wherein.

DETAILED DESCRIPTION

Figure 1:
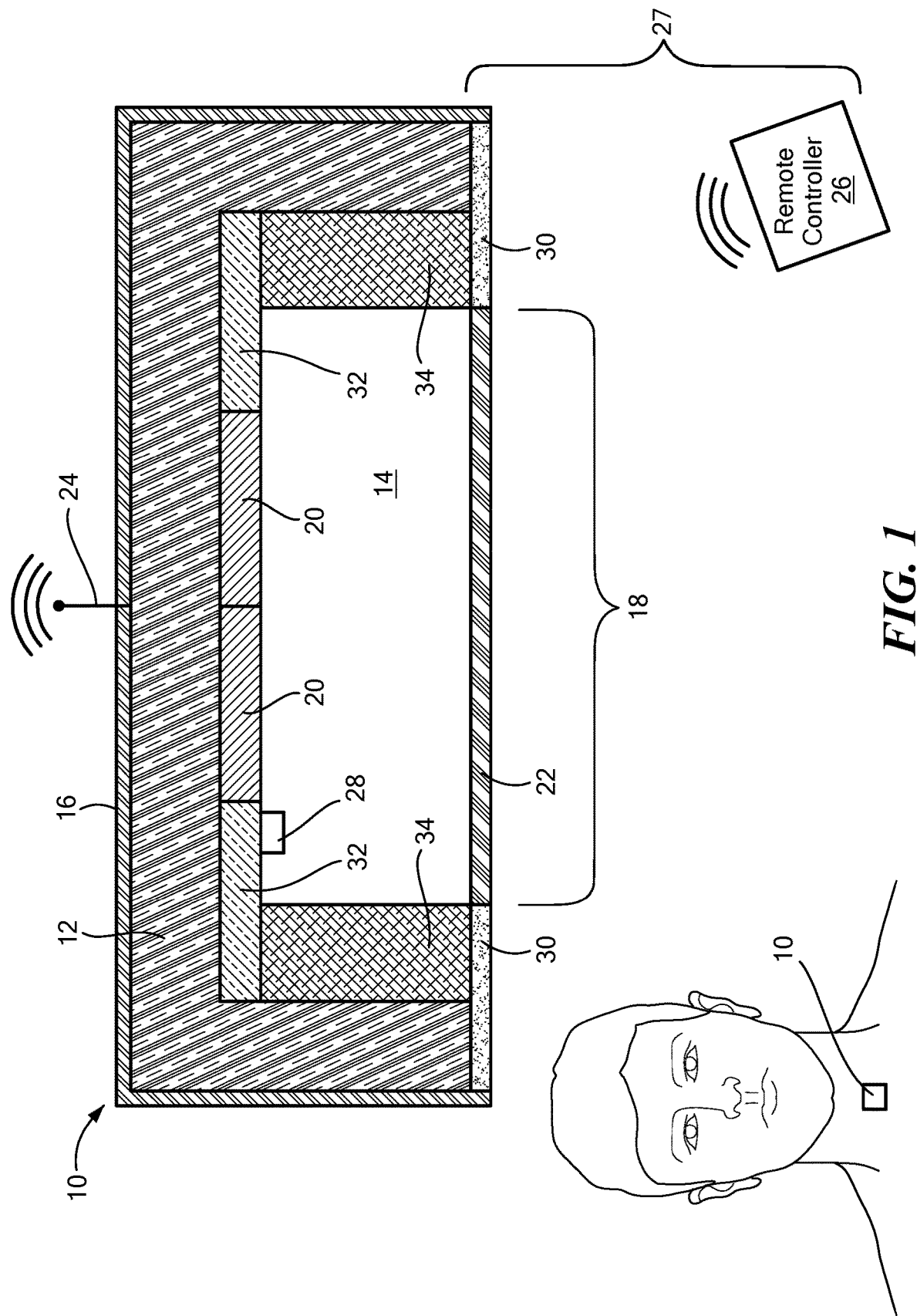
FIG. 1 is a cross-sectional view of embodiment of an acoustic sensor constructed in accordance of the principles of the present application and a view of the acoustic sensor coupled to a patient's body.
Figure 2:
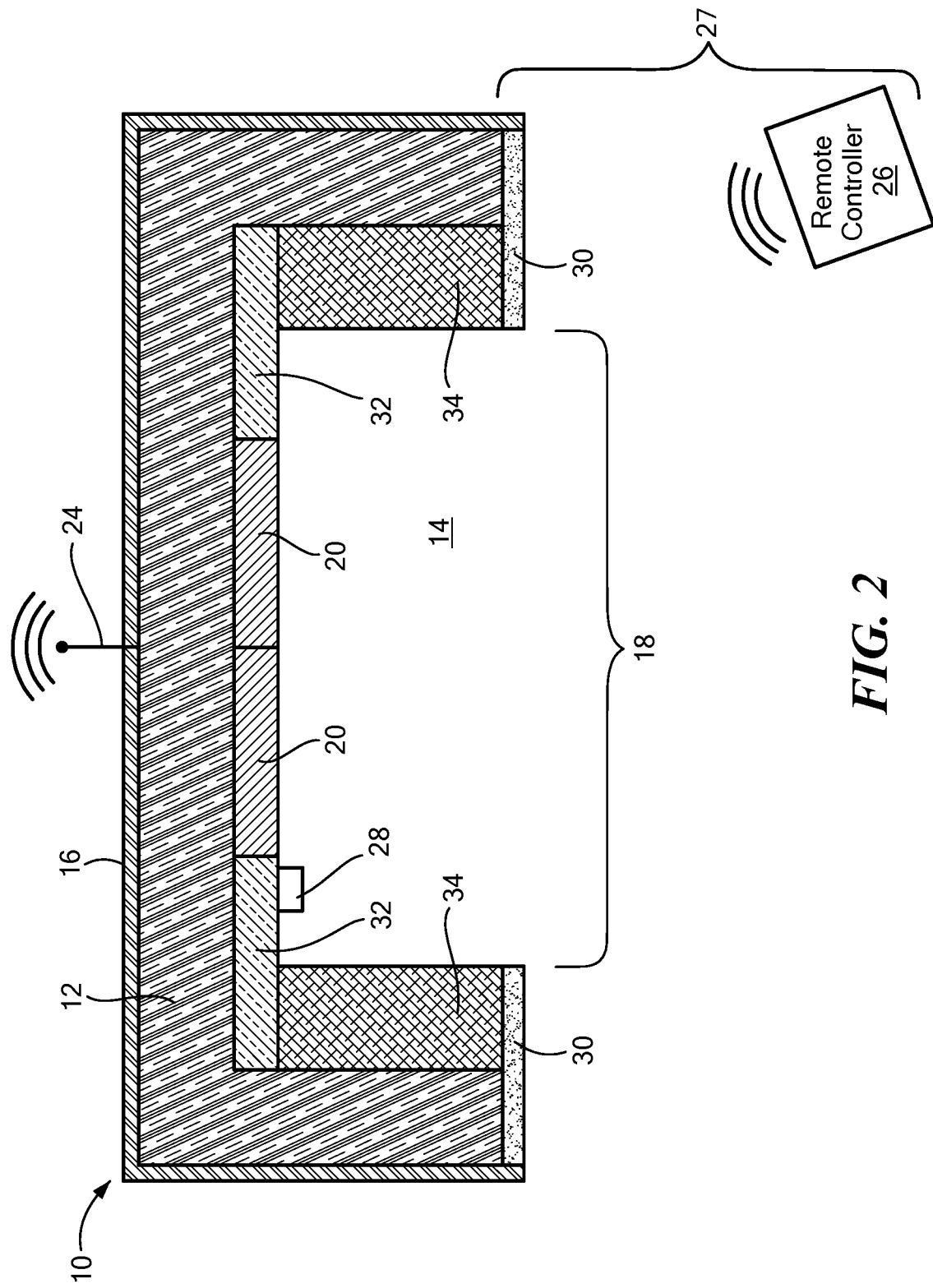
FIG. 2 is a cross-sectional view of another embodiment of an acoustic sensor constructed in accordance of the principles of the present application.
Figure 3:
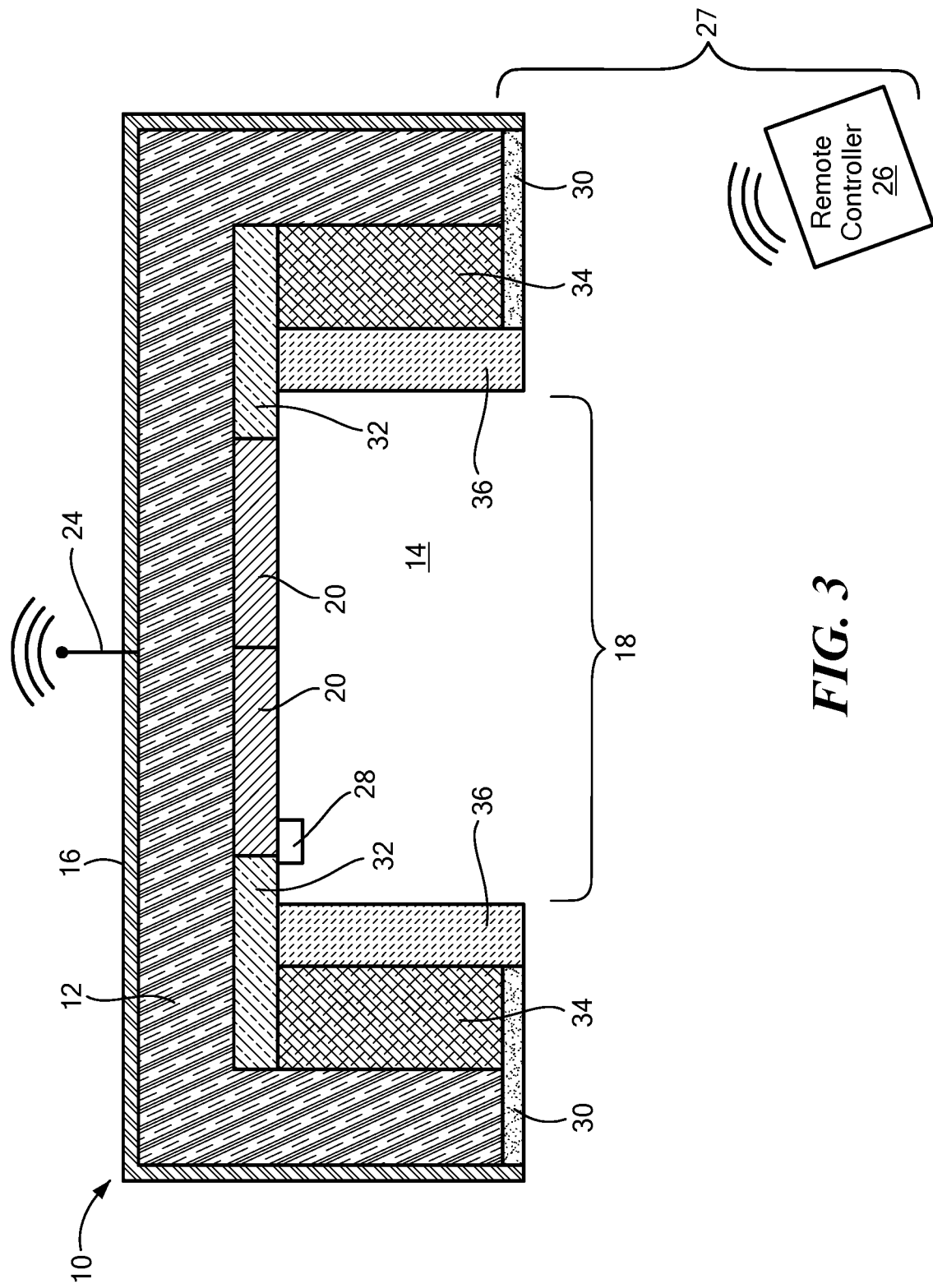
FIG. 3 is a cross-sectional view of another embodiment of an acoustic sensor constructed in accordance of the principles of the present application.
Figure 4:
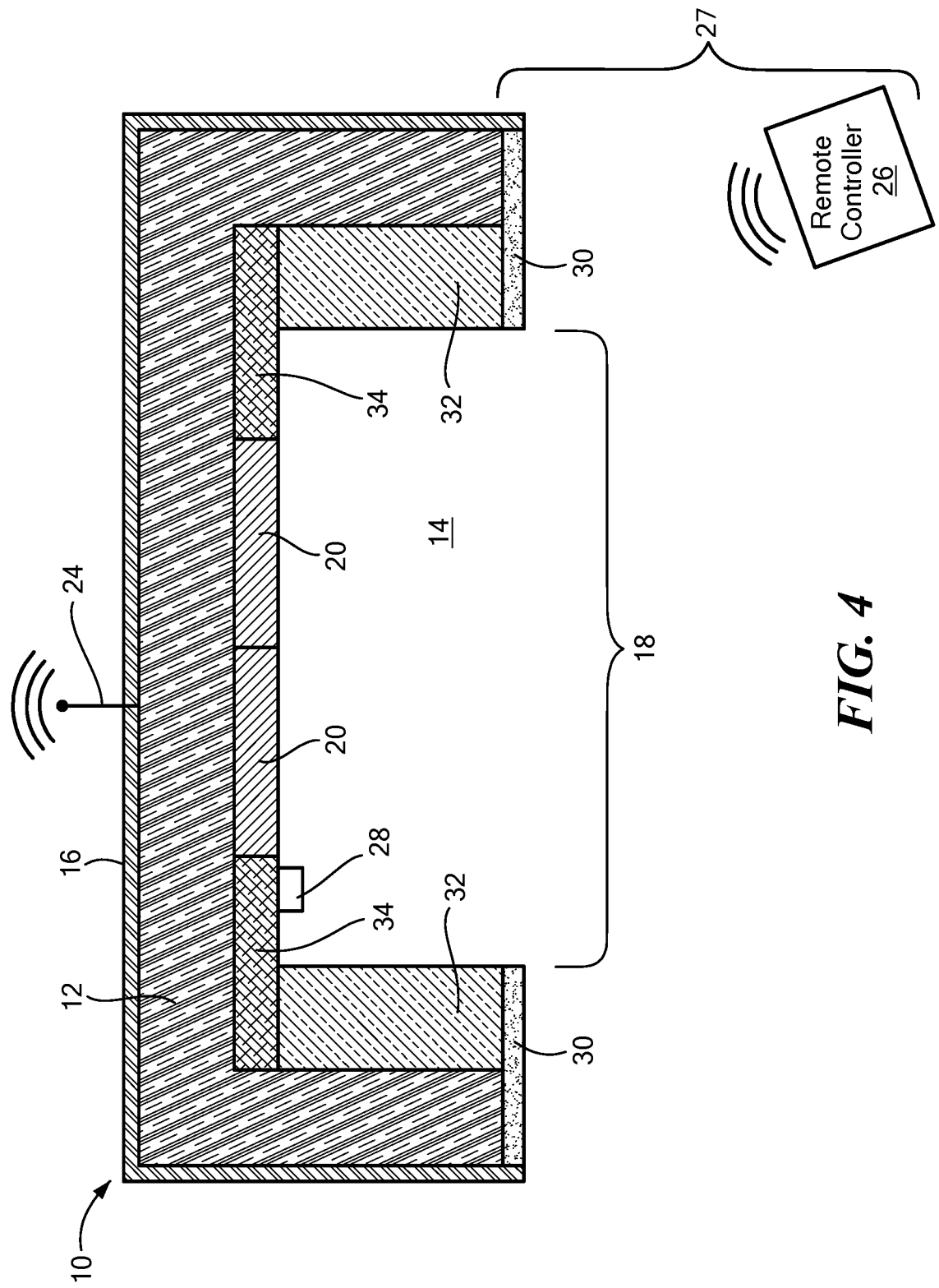
FIG. 4 is a cross-sectional view of another embodiment of an acoustic sensor constructed in accordance of the principles of the present application.

Before describing in detail exemplary embodiments, it is noted that the embodiments reside primarily in combinations of apparatus components and processing steps related to an acoustic sensor system and related method thereof. Accordingly, the system and method components have been represented where appropriate by conventional symbols in the drawings, showing only those specific details that are pertinent to understanding the embodiments of the present disclosure so as not to obscure the disclosure with details that may be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It may be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It may be further understood that terms used herein should be interpreted as having a meaning that is consistent with their meaning in the context of this specification and the relevant art and may not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art may appreciate that multiple components may interoperate and modifications and variations are possible of achieving the electrical and data communication.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

With reference to FIGS. 1-6, an acoustic measurement device or TSD 10 is depicted which is sized and configured to be releasably affixed to the skin of a mammal. The device 10 includes a housing 12 defining an at least partially enclosed chamber 14 therein. In one configuration, the housing 12 defines a width and a length of 2 cm or less. For example, the housing 12 may be substantially cube shaped having a width of 2 cm or less, such as between 0.5 cm to 2.5 cm, a sphere or disc having a diameter of 2 cm or less, or another shape suitable for affixing to the patient.

The housing 12 may be composed of one or more materials, such as a lightweight plastic, metal, ceramic, or composite having integrated or added sound insulation material 16 on an exterior thereof, lining the interior of the chamber 14, or both, to attenuate ambient sound. The walls of the housing and lining may be separated by an air-filled space designed to attenuate ambient sound. The housing 12 may be manufactured from materials and structure that attenuates transmission of ambient sound into the chamber 14. In one configuration, an airtight seal is formed between the housing 12 and skin surface to isolate the inside of the TSD 10 from the external environment. In an alternative configuration, the housing 12 may be porous or have an external opening such that sound may penetrate the housing 12 from an ambient environment, depending on the application. In one configuration, the housing 12 defines a single opening 18 to provide access to the chamber 14; however, the number and size of the openings 18 are not limited to a particular number and size. The sound insulation material 16 may surround the housing 12 in all areas with the exception of around the opening 18. The housing 12 may define a dome shape, bell shape, (FIG. 6) or any shape such that the chamber 14 is isolated from external sounds and optimized to measure the sounds of air movement within the trachea.

One or more sound transducers 20 may be affixed, either permanently or removably, within the chamber 14 of the housing 12 for measuring at least one of a respiratory rate and a tidal volume of the patient. The sound transducer 20 may be one or more microphones, for example, in the 20-2000 Hz range, configured to measure sound energy within the chamber 14 and transduce an acoustic signal into a digital signal. The miniature electronic microphones (electric, piezoelectric, or MEMS) transduce the mechanical vibrations caused by airflow within the proximal trachea during inhalation and exhalation with a high signal-to-noise ratio. In one configuration, the sound transducer 20 is located at an end of the housing 12 opposite an end of the housing 12 defining the opening 18 and may be suspended within the chamber 14 using, for example, an elongate rod or other suspension element (not shown) extending from the interior surface of the chamber 14 such that the sound transducer 20 is not in contact with the interior walls of the housing 12.

A flexible diaphragm 22 may be disposed within the opening 18 that is coextensive or slightly recessed within a surface of the housing 12. The diaphragm 22 may be a thin flexible material that resonates in response to sound energy, for example airflow through the trachea of a mammal, in a manner similar to a pediatric stethoscope head. In one configuration, the diaphragm 22 is electrically coupled to the sound transducer 20 such that when the diaphragm 22 resonates, the sound vibration is directly measured by the sound transducer 20. In other configurations, rather than being coupled to the diaphragm 22, the sound transducer 20 is in close proximity to the diaphragm 22, for example, immediately adjacent thereto to minimize any ambient sound measured by the sound transducer 20. In other configurations, the diaphragm 22 is the actual diaphragm of the sound transducer 20 and is directly coupled to an electromagnetic coil, capacitor, or piezoelectric crystal of the sound transducer 20. In one configuration, the interior of the housing 12 may define a curved semi-circle, dome, or other shape to focus the sound energy transduced from the skin surface directly into the diaphragm 22. For example, the sound transducer 20 and diaphragm 22 may be angled and positioned in a manner to measure sounds of the airflow as it enters and exits the larynx. In other configurations, the sound transducer 20 and the diaphragm 22 are aimed toward the airflow through the trachea.

Continuing to refer to FIGS. 1-6, a wireless transmitter 24 may be coupled to the housing 12, which is in communication with the sound transducer 20. The wireless transmitter 24, which may transmit and receive, is configured to transmit the transduced acoustic signal measured by the sound transducer 20. In one configuration, the wireless transmitter 24 is included as part of a processing circuitry having one or more processors included within the housing 12. For example, the wireless transmitter 24 may transmit the measurement of the respiratory rate, the tidal volume, the heart rate, or other vital sign data, to a remote controller 26 which forms the AVMS 27 in combination with the TSD 10. The remote controller 26 may be in the form of a smartphone, tablet, smartwatch, Echo™ device, Alexa™ device, cable box, or other mobile communication device configured to be held, coupled to, or in proximity to the patient, that communicates with the device 10 by Bluetooth® or WiFi®, or another electronic handshake such that acoustic information may be relayed to the controller 26 for real-time processing. The controller 26 may further include processing circuitry with one or more processors to process the data received from the TSD 10. The results of such processing may be displayed on the display of the controller 26 or transmitted by the controller 26 to a remote location for further processing and/or analysis.

The wireless transmitter 24 and the sound transducer 20 may be powered by a same rechargeable power source 28, for example, a rechargeable battery. The power source 28 may be charged by induction or wirelessly, thereby remaining coupled to the device 10 during charging. In other configurations, the sound transducer 20 and wireless transmitter 24 may have separate power sources. Although the power source 28 is shown as being smaller size wise relative to some other components of device 10 disclosed herein, it is noted that the illustrated size of the power source 28 is merely exemplary and may be any shape or size.

Referring back to FIG. 1, the TSD 10 may include an adhesive 30 adhered to the patient's skin proximate one of the tracheal notch or a lateral neck region of the patient to measure sound and/or vibrations associated with the patient's breathing. The adhesive 30 may also at least partially surround the opening 18. The adhesive 30 may be a double-sided tape or pad or other removable adhesive which allows the device 10 to be releasably adhered to the skin of the patient after remaining affixed to the patient for a predetermined period of time, for example, 3-14 days. In one configuration, the adhesive 30 surrounds the opening 18 on the surface of the housing 12 without occluding or otherwise blocking the opening 18 to avoid interfering with sound waves entering the chamber 14.

In an exemplary configuration, the controller 26 is configured to compare the measurement of at least one of the respiratory rate and the tidal volume to a respective predetermined threshold, which may be a range or value, or patient baseline with the RIS discussed above. For example, the average respiratory rate for a sedentary person is approximately 12-15 breaths per minute. A typical inhalation(inspiration) period is approximately 1 second, followed by a 2 second pause, followed by a 2 second period of exhalation(expiration). The period of exhalation is always longer than the period of inhalation. Faster respiratory rates decrease the amount of time during each period of the respiratory cycle. The pause between breaths may become shorter with a rapid respiratory rate.

In contrast to the rapid respiratory rate, the amount of time during each inhalation and exhalation period increases with a slow respiratory rate, and the pause may become longer. A typical tidal volume, the amount of air moved into the body during inhalation and out of the body during exhalation, at rest, is approximately 500 ml/breath. Thus, at rest, a typical person has a minute ventilation of approximately 6000 ml/minute (12 breaths/min×500 ml tidal volume/breath=6 L/min). Physiologists have determined the normal range of respiratory rate, tidal volume, and minute ventilation at rest and during activity for neonates, children, adolescents, adults, and geriatric adults based on height, weight, age, and gender. Based on these predetermined known parameters, the controller 26 is configured to determine an adverse event, such as hypoventilation caused by a drug overdose, in real time, if the measurement of at least one of the respiratory rate and the tidal volume falls outside of a respective predetermined range by a predetermined amount.

For example, controller 26 may establish an adverse event risk index score (RIS), which may be a predetermined range, based on the percentage change, absolute change, or rate of change from predetermined known parameters or baseline. For example, the percentage change may be between 5%-50%, or more, from the predetermined known parameters. Such a percentage is merely exemplary and may be set by a clinician based on the patient's own tidal volume and/or respiratory rate measurements when active and when at rest and the controller 26 may be configured to change the patient's baseline based on observed breathing patterns. For example, the controller 26 may employ algorithms (machine-learning, deep learning, artificial intelligence, and/or neural networks) to recognize a distinct pattern from the patient's usual baseline pattern. In one example, hypoventilation may cause higher levels of arterial carbon dioxide, which in turn produces greater sedation, less movement, snoring, head bobbing, uncoordinated movements, which can be detected by an activity sensor/accelerometer, described in more detail below. For example, a risk index score of "30" could produce an alert, a risk index score of "40" could produce a warning, and a risk index score >"50" could produce an alarm and/or an automated injection of an opioid reversal medication (for example, Naloxone or Narcan). Also, for example, the device 10 could produce a low alert with a 20-30% change of RR and/or TV suggesting impending hypoventilation, a medium alert with a 30-50% change, and a red alert/alarm with >50% change from baseline. The AVMS 27 may have threshold alerts/alarms and predictive alerts/alarms that warn the patient and/or clinician of an increased risk for an adverse event and/or a serious adverse event with a negative clinical outcome.

As mentioned above, adverse events may include hypoventilation, which is defined as an elevated partial pressure of carbon dioxide in the blood (PaCO2>45 mm Hg) due to insufficient minute ventilation relative to the metabolic production of CO2. In addition, such adverse events may include hyperventilation which is defined as a decreased partial pressure of carbon dioxide in the blood (PaCO2<35 mm Hg) due to excessive minute ventilation relative to the metabolic production of CO2, hypopnea which is defined as overly shallow breathing or an abnormally low respiratory rate, bradypnea which is defined as abnormally slow respiratory rate, hyperpnea which is defined as an increased depth and rate of breathing, tachypnea which is defined as an abnormally rapid respiratory rate, and apnea which is defined as a pause in breathing where there is no movement of the muscles of inhalation and the volume of the lungs remain unchanged.

The controller 26 may apply low pass and high pass filters to the measured data to filter out anomalous data and ambient noise. An external microphone may be used for ambient noise suppression and noise cancelling. In one configuration, tracheal sounds may be analyzed by the controller 26 using frequency versus time curves and amplitude versus time curves to diagnose a normal pattern of inhalation and a normal pattern of exhalation (i.e., clear uninterrupted sound patterns) relative to abnormal inhalation/exhalation sounds or sound patterns. Sleep apnea and other pathological conditions of the brain and upper airway commonly cause intermittent upper airway obstruction that can lead to hypoventilation, hypoxemia, arrhythmias, pulmonary hypertension, and heart failure. Opioids, alcohol, illegal drugs, or medications that cause sedation, relax the upper airway muscles, leading to mild, moderate, or severe upper airway obstruction (snoring and obstructive apnea). As such, analysis of the partially obstructed upper airway sound patterns can be used to diagnose the progression of airway muscle relaxation as an estimate of the severity of sleep apnea or the degree of central nervous system sedation.

Continuing to refer to FIGS. 1-6, the device 10 may further include an accelerometer 32, a temperature sensor 34, and/or a reflectance pulse oximeter 36, which may be positioned within the housing 12 and coupled to the power source 28 in communication with the controller 26. The 3-axis accelerometer 32 may be configured to measure a relative x-y-z position and a movement of the patient, such as the amount and pattern of head bobbing, body movement, body coordination, and body position in real-time to further estimate, in the case of a drug overdose, the degree of sedation and the trends of sedation over time. The accelerometer 32 also senses chest wall movement to monitor the onset/timing of inhalation and exhalation. The temperature sensor 34 may be integrated within the housing and used to detect a decrease or increase in body temperature. The reflectance pulse oximeter 36 may be configured to monitor percent hemoglobin oxygen saturation and the photoplethysmograph waveform, whether continuously, intermittently, or when the algorithm detects/predicts the onset of hypoventilation or a change in health. The pulse oximeter's waveform can be analyzed in real-time to estimate heart rate, heart rate variability, stroke volume, stroke volume variability, pre-load, myocardial contractility, systemic vascular resistance, cardiac output, and systemic blood pressure.

In one configuration, the device 10 may also measure the patient's cardiac electrogram or electrocardiogram to determine the real-time heart rate and heart rhythm. For example, the device 10 may include a plurality of electrodes 38 (FIG. 11) positioned on, for example, a portion of the housing 12 in contact with the patient's skin to measure the patient's electrocardiogram. The method of pulse-transit time can utilize the electrocardiogram signal and the pulse oximeter 36 plethysmograph signal to calculate the systemic blood pressure. The electrocardiogram and pulse oximeter signals measured by the TSD 10 worn on the body may communicate wirelessly with the ambulatory patient's smart watch that also contains skin electrodes that measure the electrocardiogram and pulse oximeter signals at the wrist, to enhance the signal-to-noise ratio and clinical performance.

In one configuration, the device 10 may also measure the patient's cardiac electrogram or electrocardiogram to determine the real-time heart rate and heart rhythm. For example, the device 10 may include a plurality of electrodes 38 (FIG. 11) positioned on, for example, a portion of the housing 12 in contact with the patient's skin to measure the patient's electrocardiogram. The method of pulse-transit time can utilize the electrocardiogram signal and the pulse oximeter 36 plethysmograph signal to calculate the systemic blood pressure. The electrocardiogram and pulse oximeter signal may communicate wirelessly with an electrocardiogram and pulse oximeter signal on the ambulatory patient's smart wrist watch to enhance the signal-to-noise ratio and clinical performance.

Figure 5:
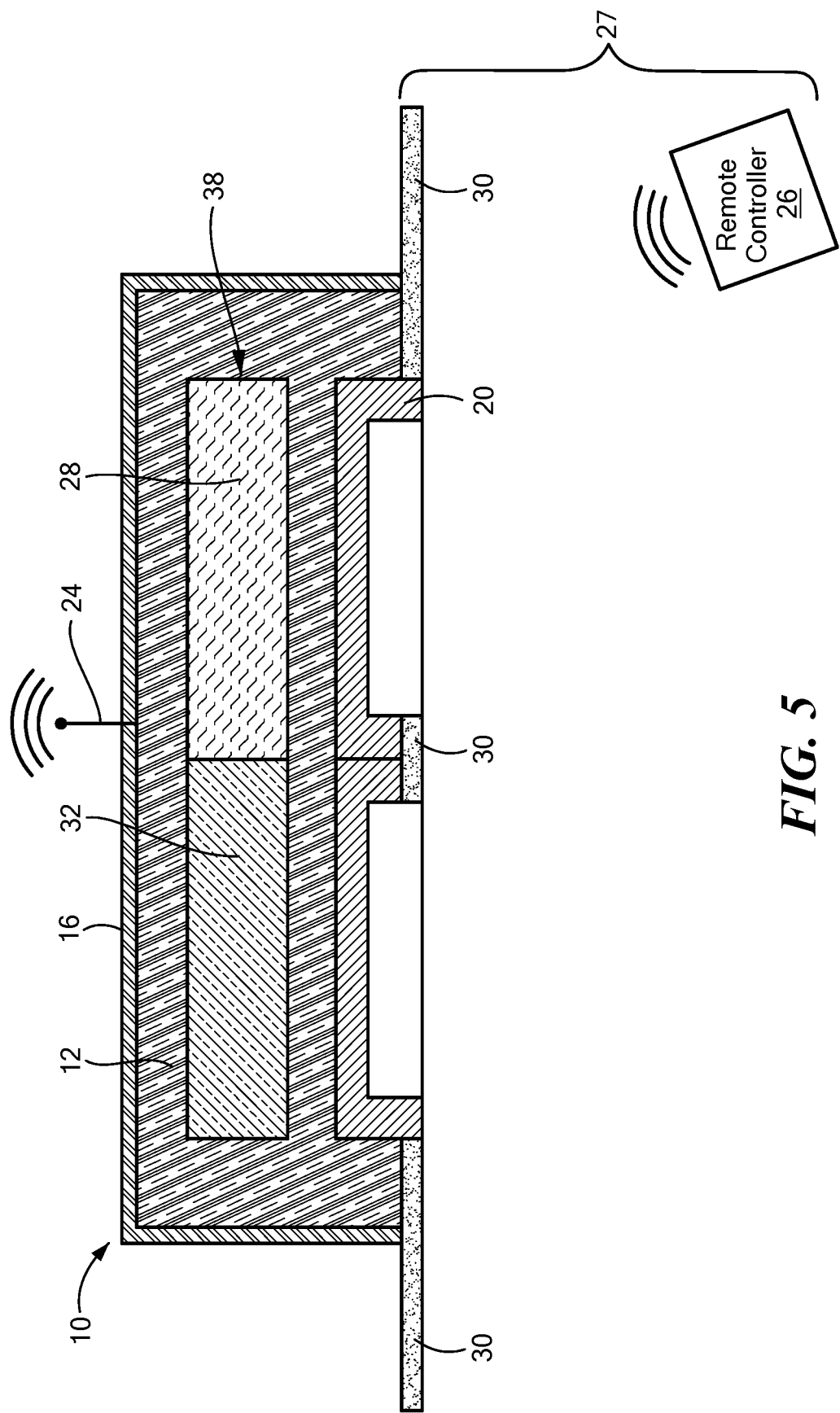
FIG. 5 is a cross-sectional view of another embodiment of an acoustic sensor constructed in accordance of the principles of the present application.
Figure 6:
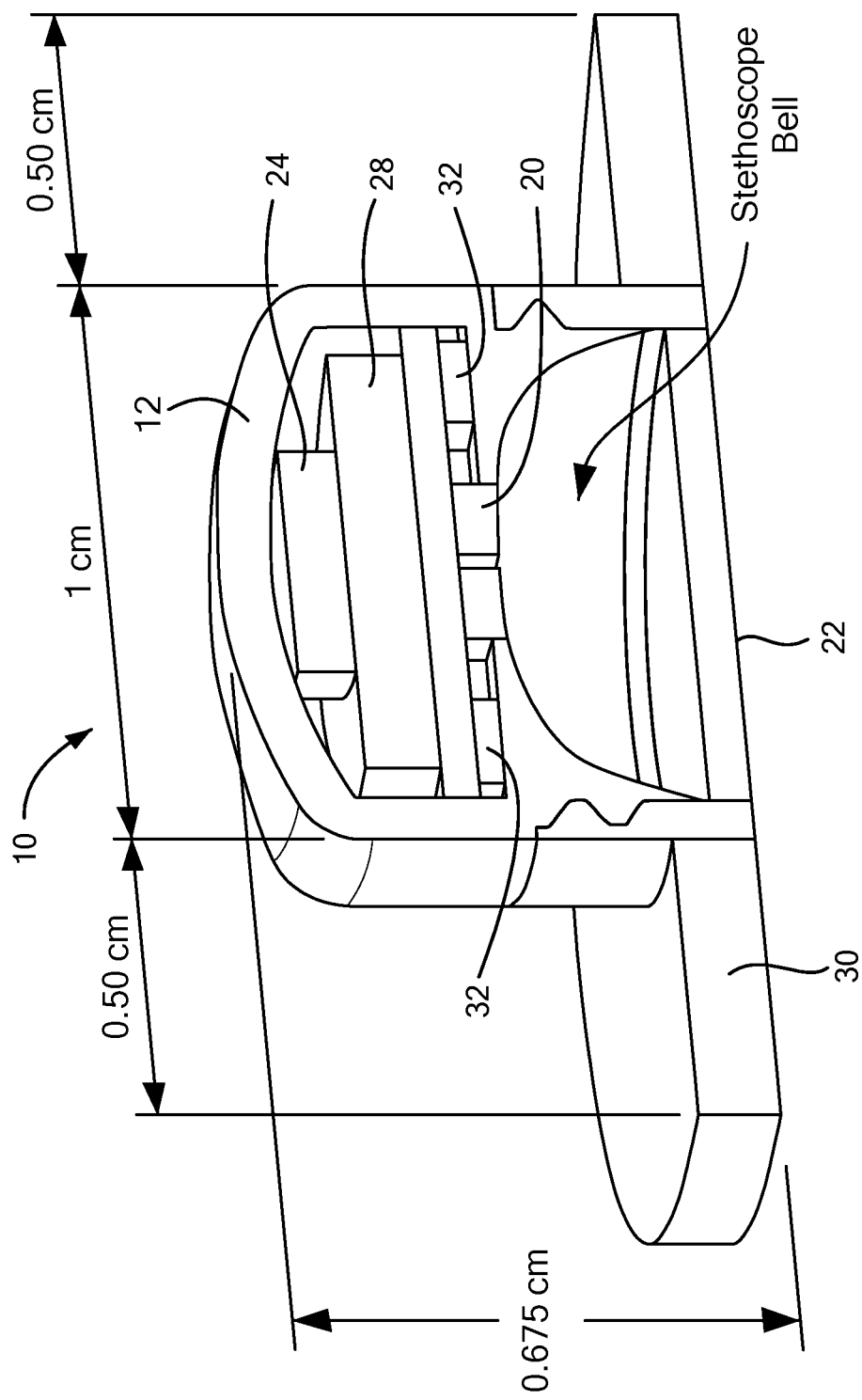
FIG. 6 is another a cross-sectional view of embodiment of an acoustic sensor constructed in accordance of the principles of the present application.

Referring now to FIG. 5, in another configuration, the sound transducer 20 may include a vibration sensor (electric, piezoelectric, or MEMS) configured to measure vibrations as a result of air flowing into and out of the trachea or lungs. The sound transducer 20 may be substantially planar with the skin of the patient to increase mechanical coupling and sensitivity. The vibration sensor accelerometer 32 and the power source 28 may be integrated into the housing 12. For example, a MEMS device may be integrated within a first chamber 38 of the housing 12 separated from the sound transducer 20. The MEMS device may further be configured to process information from one or more of the sensors disclosed herein which may be included in this configuration. The MEMS device may be included in any of the embodiments discussed above.

Figure 7:
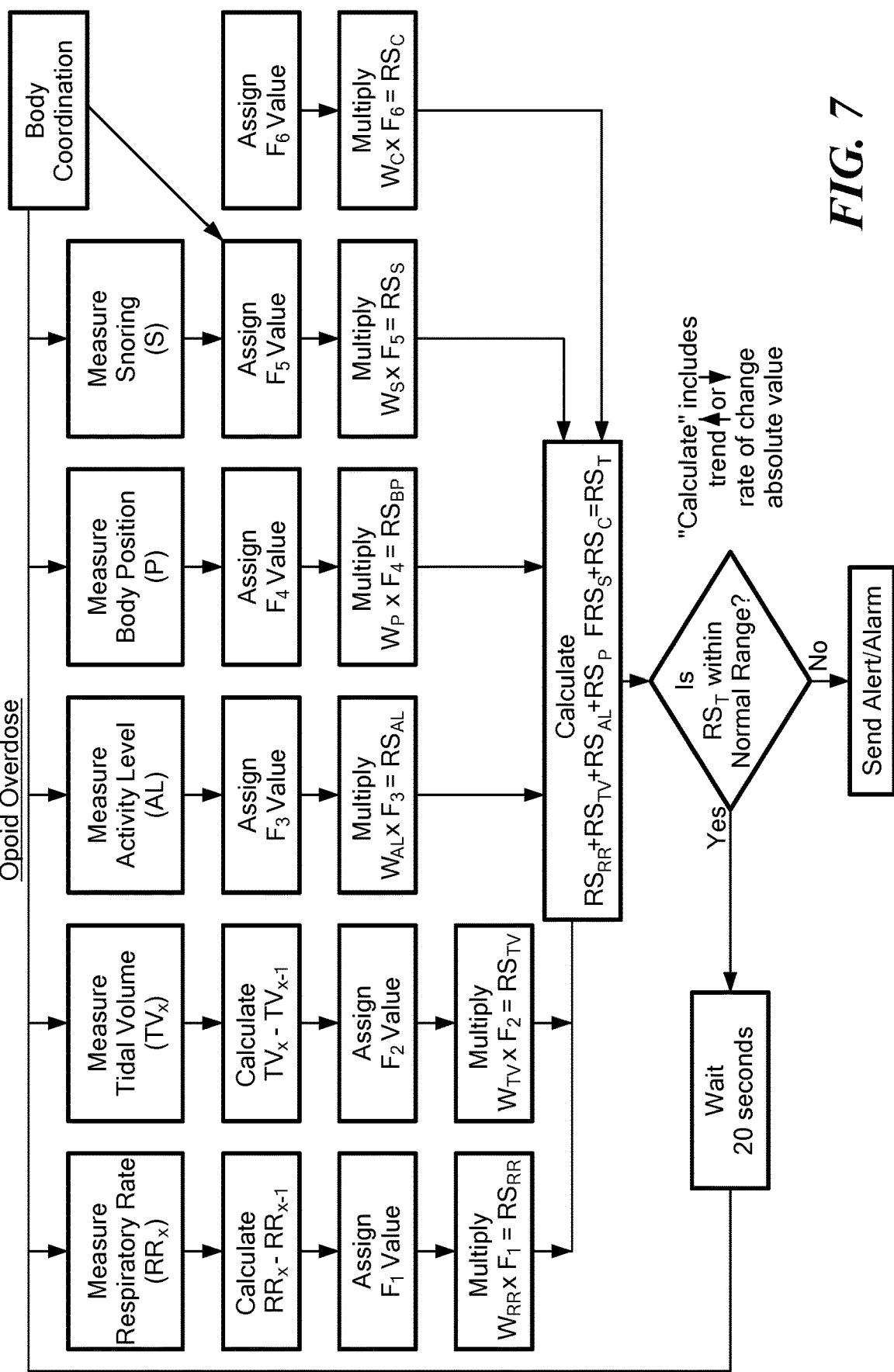
FIG. 7 is a flow chart showing exemplary steps of determining a patient's risk index score for an opioid overdose in accordance with an embodiment of the present application.

Referring now to FIG. 7, as discussed above, the controller 26 may employ a method to assign a risk index score to a wearer of the device 10, such risks may include as discussed above an opioid overdose. The method includes continuously, intermittently, or continually measuring the RR and TV of the patient wearing the device 10. In one configuration, the controller 26 further measures at least one from the group consisting of the user's activity level (AL), body position (P), snoring sounds (S), and body coordination (BC). The controller 26 may then further calculate the user's absolute RIS using the values for RR, TV TD, AL, P, S, and/or BC, the direction trend of each value over time, and the rate of change of each value and the sum of all the values to establish a predictive score for an opioid overdose. The absolute RIS may be calculated and updated every 20 to 30 seconds, or any periodic or continual interval. Alerts and alarms may be based upon the absolute RIS number, the RIS direction of change, and the RIS rate of change over time.

For example, the AVMS may continuously measure the RR and TV and the controller 26 may calculate the averaged RR and TV over a predetermined period of time (x), for example each 20 to 30 second interval. The controller 26 may then assign a risk value represented as a value (F), to score that particular parameter based on a predefined scale and determine if an alert (warning) or an alarm (urgent) is to be generated. For example, as shown in TABLE 1, a respiratory rate (RR) of 15 to 14 breaths/minute is assigned an F value of zero to −4 (low risk), a RR of 7 to 6 breaths/minute is assigned an F value of +8 (high risk), and a RR of 6 to 5 breaths/minute is assigned an F value of +10 (higher risk). One potential reason as to why RR would decrease is owing to an increased number of opioid molecules attached to opioid receptors in the midbrain. Opioids cause the RR to decrease from an average 15±3 breaths/minute at rest. Opioids also cause the TV to decrease from an average 7 ml/kg at rest. Higher opioid receptor binding causes a more severe and progressive decrease in the RR and TV over time. An opioid overdose can occur quickly when a large amount of opioid reaches the midbrain opioid receptors quickly after a large oral dose or after an intravenous injection. In one example, the controller 26 may trigger an alert, which may indicate caution as the absolute value of RR rate drops to a first predetermined rate, or an alarm to trigger immediate action when the RR drops below a second predetermined rate.

TABLE 1

| Absolute RR in breaths/minute and the corresponding F value | | | | | | | | | | | | | | | |
|---|---|---|---|---|---|---|---|---|---|---|---|---|---|---|---|
| 15-14 | 14-13 | 13-12 | 12-11 | 11-10 | 10-9 | 9-8 | 8-7 | 7-6 | 6-5 | 5-4 | 4-3 | 3-2 | 2-1 | 1-0 | 0 |
| −4 | 0 | 0 | +1 Alert | +2 | +3 Alert | +4 | +5 Alert | +8 | +10 Alarm | +12 | +16 Alarm | +20 | +30 Alarm | +30 | +30 |

In addition to the absolute RR discussed above and the resulting F value, the controller 26 may further calculate the RR direction of change, symbolized by the up or down arrows in TABLE 2 below, and the rate of change of the RR, and multiply those F values with weighting factors. The controller 26 may automatically adjust the weighting factor over time in response the patient's previously analyzed RR trend data, to optimize the sensitivity and specificity for detecting and predicting the progression from mild, to moderate, to severe hypoventilation. For example, the F value for RR may comprise three factors, namely, change in absolute RR, the direction of RR, and the rate of change of RR. The direction and rate of change of RR optionally may have a weighting factor (W) on the score, for example, 2× or 3×, or any multiple. In one example, FRR=(Fabsolute RR+2$F_{RR\ direction}$+3$F_{RR\ rate\ of\ change}$). An increased number of opioid molecules attached to opioid receptors in the midbrain cause the RR to decrease from an average range of 15±3 breaths/minute. Higher opioid receptor binding causes a progressive decrease in the RR over time. An opioid overdose can occur quickly when a large amount of opioid reaches the midbrain receptors quickly after a large oral dose, an intravenous injection, or combined with alcohol, benzodiazepams, or other respiratory depressant medications This may cause the RR to become more variable with a slow or fast rate of decrease over a longer period of time. The ingestion of alcohol and other drugs may worsen the respiratory and cardiovascular affects when combined with the opioids.

The RIS for opioid induced hypoventilation has a more positive value (+ more risk) when there is a decrease in the RR over time. There is a higher risk during a rapid decrease in RR over time. The RIS for opioid induced hypoventilation has a more negative value (− less risk) when there is an increase in RR over time. There is a lower risk during a rapid increase in RR over time. There is a non-linear increase in risk points when the RR decreases into the clinically significant range. The controller 26 recognizes the vital sign pattern towards hypoventilation early enough to prevent a permanent injury or death due to respiratory acidosis and hypoxemia. The middle column of TABLE 2 may be used for adult patients with average sensitivity to opioid induced respiratory depression. The left column may be used for patients with low sensitivity to opioid induced respiratory depression. The right column may be used for patients with high sensitivity to opioid induced respiratory depression.

TABLE 2

| RR direction and rate of change and corresponding F values for three different patient sensitives to opioid induced respiration depression. | | | | |
|---|---|---|---|---|
| Respiratory Rate (RR) Direction and Rate of Change | Low Sensitivity Points | Average Sensitivity Points | High Sensitivity Points | |
| Rapid Decrease RR ↓↓ | +4 | +6 | +8 | Alarm |
| Slow Decrease RR ↓ | +2 | +3 | +4 | Alert |
| No Change RR → | 0 | 0 | 0 | |

TABLE 2-continued

| RR direction and rate of change and corresponding F values for three different patient sensitives to opioid induced respiration depression. | | | |
|---|---|---|---|
| Respiratory Rate (RR) Direction and Rate of Change | Low Sensitivity Points | Average Sensitivity Points | High Sensitivity Points |
| Slow Increase RR ↑ | −2 | −3 | −4 |
| Rapid Increase RR ↑↑ | −4 | −6 | −8 |

EXAMPLES:

1. RR that is rapidly decreasing (+4) from 9 to 8 breaths/minute (+2) increases the risk index score +6
2. RR that is rapidly decreasing (+4) from 8 to 7 breaths/minute (+3) increases the risk index score +7
3. RR that is slowly decreasing (+2) from 7 to 6 breaths/minute (+5) increases the risk index score +7
4. RR that is rapidly increasing (−4) from 6 to 7 breaths/minute (+5) increases the risk index score +1
5. RR that is slowly decreasing (+2) from 12 to 11 breaths/minute (+1) increases the risk index score +3

In addition to scoring the patient's RR, the controller 26 further analyzes the patient's TV in a similar manner to that of RR rate. An increased number of opioid molecules attached to opioid receptors in the midbrain cause the TV to decrease from an average range of 500±50 ml/breath (~7 ml/kg). Higher opioid receptor binding causes a progressive decrease in the TV over time. Hypoventilation and hypoxia owing to an opioid overdose can occur quickly when a large amount of opioid reaches the midbrain opioid receptors quickly after a large oral dose or an intravenous injection. The majority of opioid overdoses occur more slowly, over a one to two-hour period. The ingestion of alcohol and other drugs may worsen the respiratory and cardiovascular affects when combined with the opioids. TABLE 3 below shows the absolute F values for changes of TV of an example patient weighing 70 kg. The RIS for opioid induced hypoventilation has a more positive value (+ more risk) when a lower TV than normal is measured. The RIS for opioid induced hypoventilation has a more negative value (− less risk) when a higher TV is measured. Note the non-linear increase in risk points when the TV decreases into the clinically significant range. The algorithms recognize the vital sign pattern towards hypoventilation early enough to prevent a permanent injury or death due to respiratory acidosis and hypoxemia. The F values are merely exemplary and may change based on the weight, age, and opioid sensitivity of the patient.

TABLE 3

Absolute TV in ml/kg. change in TV over a defined period of time, and the corresponding F value

| Tidal Volume (TV) (ml/kg) | Tidal Volume (TV) (ml) | Change in TV (ml/kg) | F value |
|---|---|---|---|
| 10 ml/Kg × 70 Kg | 700 ml | 10 to 9.5 | −10 |
| 9.5 ml/Kg | 665 ml | 9.5 to 9.0 | −8 |
| 9.0 ml/kg | 630 ml | 9.0 to 8.5 | −6 |
| 8.5 ml/kg | 595 ml | 8.5 to 8.0 | −4 |
| 8.0 ml/kg | 560 ml | 8.0 to 7.5 | −2 |
| 7.5 ml/kg | 525 ml | 7.5 to 7.0 | 0 |
| 7.0 ml/kg | 490 ml | 7.0 to 6.5 | 0 |
| 6.5 ml/kg | 455 ml | 6.5 to 6.0 | +2 |
| 6.0 ml/kg | 420 ml | 6.0 to 5.5 | +4 |
| 5.5 ml/kg | 385 ml | 5.5 to 5.0 | +6 |
| 5.0 ml/kg | 350 ml | 5.0 to 4.5 | +8 |
| 4.5 ml/kg | 315 ml | 4.5 to 4.0 | +10 |
| 4.0 ml/kg | 280 ml | 4.0 to 3.5 | +12 |
| 3.5 ml/kg | 245 ml | 3.5 to 3.0 | +14 |
| 3.0 ml/kg | 210 ml | 3.0 to 2.5 | +20 |
| 2.5 ml/kg | 175 ml | 2.5 to 2.0 | +30 |
| 2.0 ml/kg | 140 ml | 2.0 to 1.5 | +30 |
| 1.5 ml/kg | 105 ml | 1.5 to 1.0 | +30 |
| 1.0 ml/kg | 70 ml | 1.0 to 0.5 | +30 |
| 0.5 ml/kg | 35 ml | 0.5 to 0 | +30 |
| 0 ml/kg | 0 ml | 0 | +30 |

In addition to the absolute TV discussed above and the resulting F value, the controller 26 further calculates the TV direction of change, symbolized by the up or down arrows in TABLE 4 below, and the rate of change of the TV, with weighting factors. The controller 26 may automatically adjust the weighting factor over time in response the patient's previously analyzed TV trend data, to optimize the sensitivity and specificity for detecting and predicting the progression from mild, to moderate, to severe hypoventilation. For example, the F value for TV may comprise three factors, namely, absolute TV, direction of TV, and rate of change of TV. The direction and rate of change of TV optionally may have a weighting factor (W) on the F value, for example, 2× or 3×, or any multiple. In one example, $F_{TV} = (F_{absolute\ TV} + 2F_{TV\ direction} + 3F_{TV\ rate\ of\ change})$.

The middle column below may be used for adult patients with average sensitivity to opioid induced respiratory depression. The left column may be used for patients with low sensitivity to opioid induced respiratory depression. The right column may be used for patients with high sensitivity to opioid induced respiratory depression.

TABLE 4

TV direction and rate of change and corresponding F values for three different sensitivities to opioid induced respiration depression.

| Tidal Volume (TV) Direction and Rate of Change | Low Sensitivity Points | Average Sensitivity Points | High Sensitivity Points | |
|---|---|---|---|---|
| Rapid Decrease TV ↓↓ | +4 | +6 | +8 | Alarm |
| Slow Decrease TV ↓ | +2 | +3 | +4 | Alert |
| No Change TV → | 0 | 0 | 0 | |
| Slow Increase TV ↑ | −2 | −3 | −4 | |
| Rapid Increase TV ↑↑ | −4 | −6 | −8 | |

| | EXAMPLES: | Points |
|---|---|---|
| 1. | TV that is slowly decreasing (+3) from 7 to 6.5 ml/Kg (0) | +3 |
| 2. | TV that is rapidly decreasing (+6) from 6.5 to 6 ml/Kg (+2) | +8 |
| 3. | TV that is rapidly decreasing (+6) from 5 to 4.5 ml/Kg (+8) | +14 |
| 4. | TV that is rapidly decreasing (+6) from 4.5 ml to 4.0 mg/Kg (+10) | +16 |
| 5. | TV that is slowing increasing (−3) from 4.5 to 5 ml/Kg (+8) | +5 |
| 6. | TV that is slowly increasing (−3) from 7 to 7.5 ml/Kg (0) | −3 |
| 7. | TV that is rapidly increasing (−6) from 7 to 7.5 ml/Kg (0) | −6 |
| 8. | TV that is not increasing/decreasing (0) around 7 ml/Kg (0) | 0 |
| 9. | TV that is rapidly increasing (−6) from 7 to 7.5 ml/Kg (0) | −6 |
| 10. | TV that is rapidly increasing (−6) from 8.5 to 9 ml/Kg (6) | −12 |
| 11. | TV that is rapidly increasing (−6) from 9.5 to 10 ml/Kg (10) | −16 |

An increasing opioid concentration in the brain produces an increasing level of sedation. Ambulatory people develop a progressive decrease in the amount of activity (body movement) due to an increasing level of sedation. An increasing level of sedation also causes a change from normal coordinated body movement to uncoordinated body movement. An increasing level of sedation also causes a pattern of head nodding. A rapid increase in the concentration of brain opioid can produce a rapid decrease in the amount of body movement, change from coordinated to uncoordinated movement, onset of head nodding, and a change from standing or sitting to the supine, lateral, or prone position.

The accelerometer 32 and controller 26 monitor body activity, body position, and body coordination as an estimate of sedation level. The pattern of body activity level is continuously analyzed to detect and predict the progression from mild to moderate to severe hypoventilation due to an opioid overdose. The controller 26 analyzes the decrease in body activity level, presence of head nodding, presence of uncoordinated body movement, and change from the standing or sitting position to the supine, lateral, or prone position to calculate an RIS for detecting/predicting opioid induced hypoventilation. For example, as shown in TABLE 5, the RIS for opioid induced hypoventilation has a more positive value (+ more risk) when a decreased amount of body activity, presence of head nodding, presence of uncoordinated movement, and change from the standing or sitting position to the lateral, supine, or prone position are detected. The RIS for opioid induced hypoventilation has a more negative value (− less risk) when an increased in amount of body activity is measured. The RIS can be updated every 20-30 seconds.

TABLE 5

F values for body position.

| Body Position | Points | |
|---|---|---|
| Lying Prone | +8 | Alert |
| Lying Lateral | +4 | |
| Lying Supine | +2 | |
| Sitting | 0 | |
| Standing | −4 | |
| Walking | −6 | |

In addition to the absolute body position discussed above and the resulting F value, the controller 26 and accelerometer 32 further calculates the body position/activity level direction of change, symbolized by the up or down arrows in TABLE 6 below, and the rate of change of the body position/activity level, with weighting factors. The controller 26 may automatically adjust the weighting factor over time in response to the patient's previously analyzed body position trend data, to optimize the sensitivity and specificity for detecting and predicting the progression from mild, to moderate, to severe hypoventilation. For example, the F value for body position/activity level may comprise three factors, namely, body position, direction of body position/activity from ambulatory to stationary, and rate of change of body position/activity. The direction and rate of change of body position/activity may have a weighting factor on the F value, for example, 2× or 3×, or any multiple.

In one example, $F_{body\ position/activity} = (F_{absolute\ body\ position/activity\ level} + 2F_{body\ position/activity\ direction} + 3F_{body\ position/activity\ rate\ of\ change})$.

TABLE 6 body position/activity, direction and rate of change and corresponding F values for three different sensitivities to opioid induced respiration depression.
Body Activity (Amount of Movement)

| Direction and Rate of Change | Low Sensitivity Points | Average Sensitivity Points | High Sensitivity Points | |
|---|---|---|---|---|
| Rapid Decrease in Activity ↓↓ | +4 | +6 | +8 | Alarm |
| Slow Decrease in Activity ↓ | +2 | +3 | +4 | Alert |
| No Change in Activity → | 0 | 0 | 0 | |
| Slow Increase in Activity ↑ | −2 | −3 | −4 | |
| Rapid Increase in Activity ↑↑ | −4 | −6 | −8 | |
| No Body Motion | +15 | +15 | +15 | Alarm |
| Uncoordinated Body Motion | +4 | +4 | +4 | Alert |
| Head Nodding | +4 | +4 | +4 | Alert |

| EXAMPLES: | Points |
|---|---|
| Rapid decrease in body activity (+6), no body motion (+15), lying prone (+8) | +29 |
| Rapid decrease in body activity (+6), uncoordinated motion (+4), standing (−4) | +6 |
| Rapid decrease in body activity (+6), head nodding (+4), sitting (0) | +10 |
| Slow decrease in body activity (+3), head nodding (+4), standing (−4) | +3 |
| Slow increase in body activity (−3), walking (−6) | −9 |
| Rapid increase in body activity (−6), walking (−6) | −12 |

An increasing opioid concentration in the brain produces an increasing level of sedation and relaxation of the upper airway muscles leading to partial and/or complete upper airway obstruction. An increasing level of sedation causes a change from talking to light snoring, moderate snoring, heavy snoring, and episodes of obstructive apnea (complete airway obstruction). The sound transducer 20, accelerometer 32, and controller 26 monitor the amount of upper airway obstruction (snoring) and the number and duration of apnea episodes. The controller 26 analyzes the degree of snoring and duration of apnea to calculate the RIS for detecting/predicting opioid induced hypoventilation.

As shown in TABLE 7, the RIS for opioid induced hypoventilation has a more positive value (+ more risk) when an increase in snoring and number/duration of apnea episodes are measured. In addition to a characteristic decrease in RR and TV, opioids cause an increase in the number of apnea episodes of short or long duration. The RIS for opioid induced hypoventilation has a more negative value (− less risk) with normal breathing and talking. The real-time RIS is updated every 20-30 seconds. The controller 26 may recognize the vital sign pattern towards hypoventilation early enough to prevent a permanent injury or death due to respiratory acidosis and hypoxemia.

TABLE 7 upper airway obstruction (snoring and apnea) and examples incorporating increases and decreases in body motion, activity, and direction

| Upper Airway Obstruction (Snoring and Apnea) | Points |
|---|---|
| Apnea > 20 seconds | +20 |
| Apnea > 15 seconds | +10 |
| Heavy Snoring | +8 |
| Moderate Snoring | +4 |
| Light Snoring | +2 |
| No Snoring | 0 |
| Talking | −8 |

| EXAMPLES: | Points |
|---|---|
| Rapid decrease activity (+6), head nodding (+4), lateral position (+4), heavy snoring (+8) | +22 |
| Rapid decrease activity (+6), prone position (+8), moderate snoring (+4), apnea > 10 (+8) | +26 |
| No motion (+15), lateral position (+4), heavy snoring (+8), apnea > 20 sec (+20) | +47 |
| Slow decrease activity (+3), uncoordinated motion (+4), lateral position (+4) | +11 |
| No change activity (0), sitting (0), no snoring (0), talking (−8) | −8 |
| Slow increase activity (−3), walking (−6), talking (−8) | −17 |

Continuing to refer to FIG. 7, the F values for each of the above measured and calculated physiological conditions are correlated against a predetermined scoring system to determine if an alert (minor warning) or alarm (major warning)

are generated. For example, the controller 26 continually measures the physiological conditions of the mammal and calculates a new RIS after a predetermined period of time, for example, five seconds to a minute. The above F values for RR, TV, AL, P, S, and BC are merely exemplary and may change over times based on the normal baseline of the particular patient. Additionally, when the sum, multiplication, division, or subtraction, or other combination of the F values for RR, TV, AL, P, S , BC are calculated ($RIS_T$), and compared against a predetermined risk threshold, which may be a range or a value, the rate at which the ($RIS_T$) changes and/or the trend direction (up or down) may also trigger an alert or an alarm. For example, if the $RIS_T$ is rapidly changing and/or trending in a direction away from the predetermined risk threshold by a predetermined value, range, or other threshold, an alarm or an alert may be triggered. Thus, in one configuration, in addition to trending and rate of change factoring into each individual RR, TV, AL, P, S, and BC F values, trending and rate of change of the calculated $RIS_T$ is also contemplated by the algorithm to determine the risk of an adverse event. Moreover, the disclosure contemplates that any one of the F values alone, or in combination with any of the other values of RR, AL, P, S, and BC may form the RIS. For example, correlating the measured sound from airflow through the trachea to TV alone against a predetermined range of TV ranges or threshold may detect an adverse event.

Figure 8:
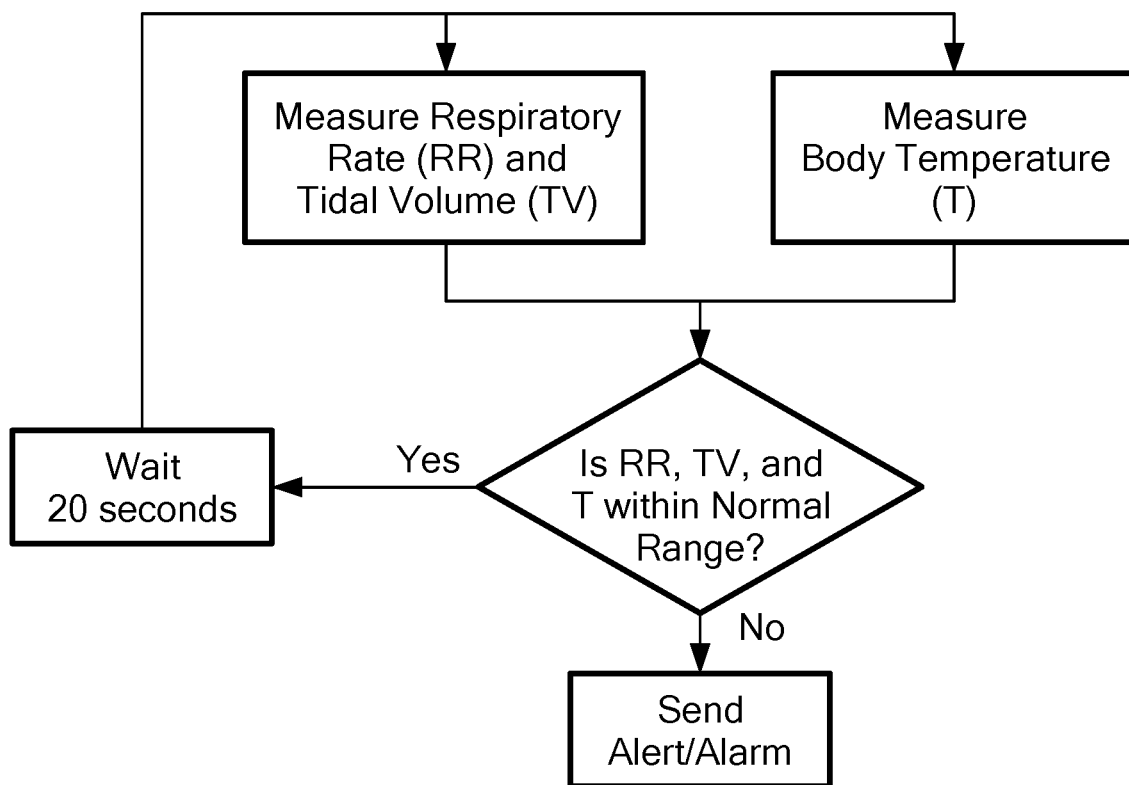
FIG. 8 is a flow chart showing exemplary steps of determining a patient's risk index score to determine a patient's risk for heat stroke or heat exhaustion.

Referring now to FIG. 8, in another method, the controller 26 is configured to predict the onset of heat exhaustion and/or heat stroke in, for example, athletes or military personnel using the RIS discussed above. The controller 26 may measure the patient's RR and or TV as discussed above with respect to the method shown in FIG. 7, including the absolute value change, direction, and rate of change of RR. The controller 26 further measures the patient's temperature with temperature sensor 34 and calculates the temperature trend and rate of change of the measured temperature similar to the methods discussed above. In another words, the controller 26 assigns an F value to the absolute measured temperature and an F score, which may be weighted to the trend (higher or lower) of the measured temperature and the rate of change. The sum of these F values, and the F values from the patient's measured RR or TV, may be compared to a threshold, and when the RIS exceeds or otherwise deviates from the threshold an alert or alarm is sounded. For example, a soldier wearing heavy clothing and a backpack on a 20-mile march may develop an increased cellular metabolism, increased CO2 production, dehydration, and increased body temperature. Compensatory mechanism may be exceeded during the march in some soldiers, leading to a rapid rise in CO2 production, a rapid rise in lactic acid (metabolic acidosis), a rapid rise in minute ventilation, and a rapid rise in body temperature (heat exhaustion and/or heat stroke).

Figure 9:
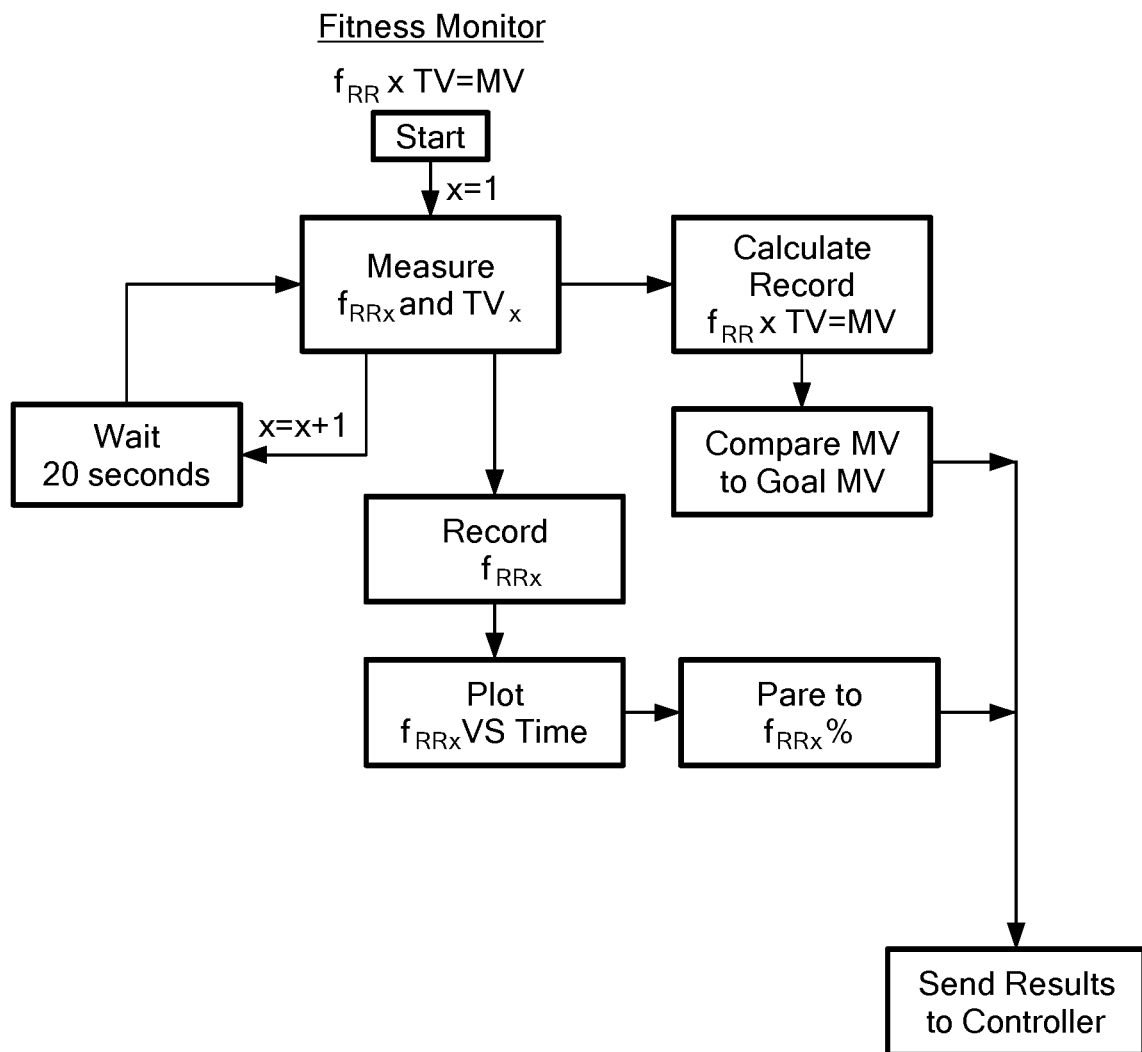
FIG. 9 is a flow chart showing exemplary steps of determining a patient's fitness level based in part on minute ventilation (MV) in accordance with an embodiment of the present application.

Referring to FIG. 9, another embodiment and application of the AVMS 27 may be employed in fitness tracking and training. It is known that respiratory function is an indicator of physical fitness. The AVMS 27 can be used to track RR, TV, and minute ventilation (MV) during mild, moderate, and heavy activity (exercise) of short or long duration. The body's response during the increased activity and during the recovery period after the activity are an estimate of health and physical fitness. These measured parameters may be paired to exercise or training time spent at optimal range, maximum minute ventilation (measure of exertion), and progress against goals among other potential analytical and statistical outputs. In other words, the measured minute ventilation, RR, and TV may be compared to a goal of minute ventilation, RR, and TV during and after the activity to determine if fitness goals are progressing. Heart rate trend measurements may be combined with MV, RR, TV, and body temperature trend measurements to enhance fitness monitor performance.

Figure 10:
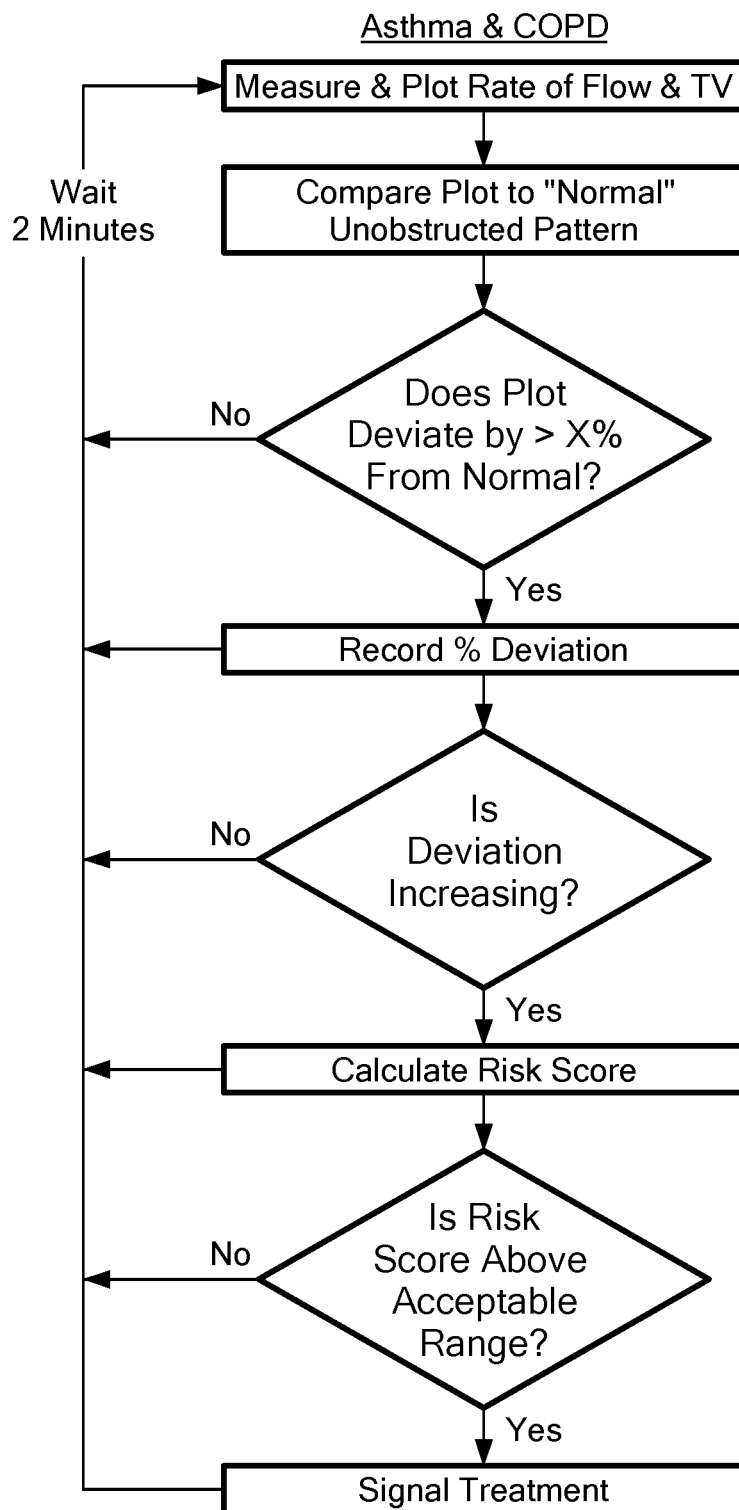
FIG. 10 is a flow chart showing exemplary steps of determining a patient's risk index score to determine a patient's risk of decompensation due to asthma and chronic obstructive pulmonary disease (COPD) in accordance with an embodiment of the present application.

Referring now to FIG. 10, similar to the algorithm shown in FIG. 7, a change from stable lung function in ambulatory patients with chronic obstructive pulmonary disease (COPD) and asthma to unstable or worsening lung function during an acute exacerbation of COPD and/or asthma may be determined by comparing known RR and TV flow rates of a particular patient or range of known values, against measured RR and TV flow rates. A RIS value that defines a clinically significant change in lung function may be assigned based on the percentage deviation from normal and the rate at which the deviation from the normal is increasing. Alarms or alerts may be generated when the RIS and the RIS trend deviates from predetermined ranges.

Figure 11:
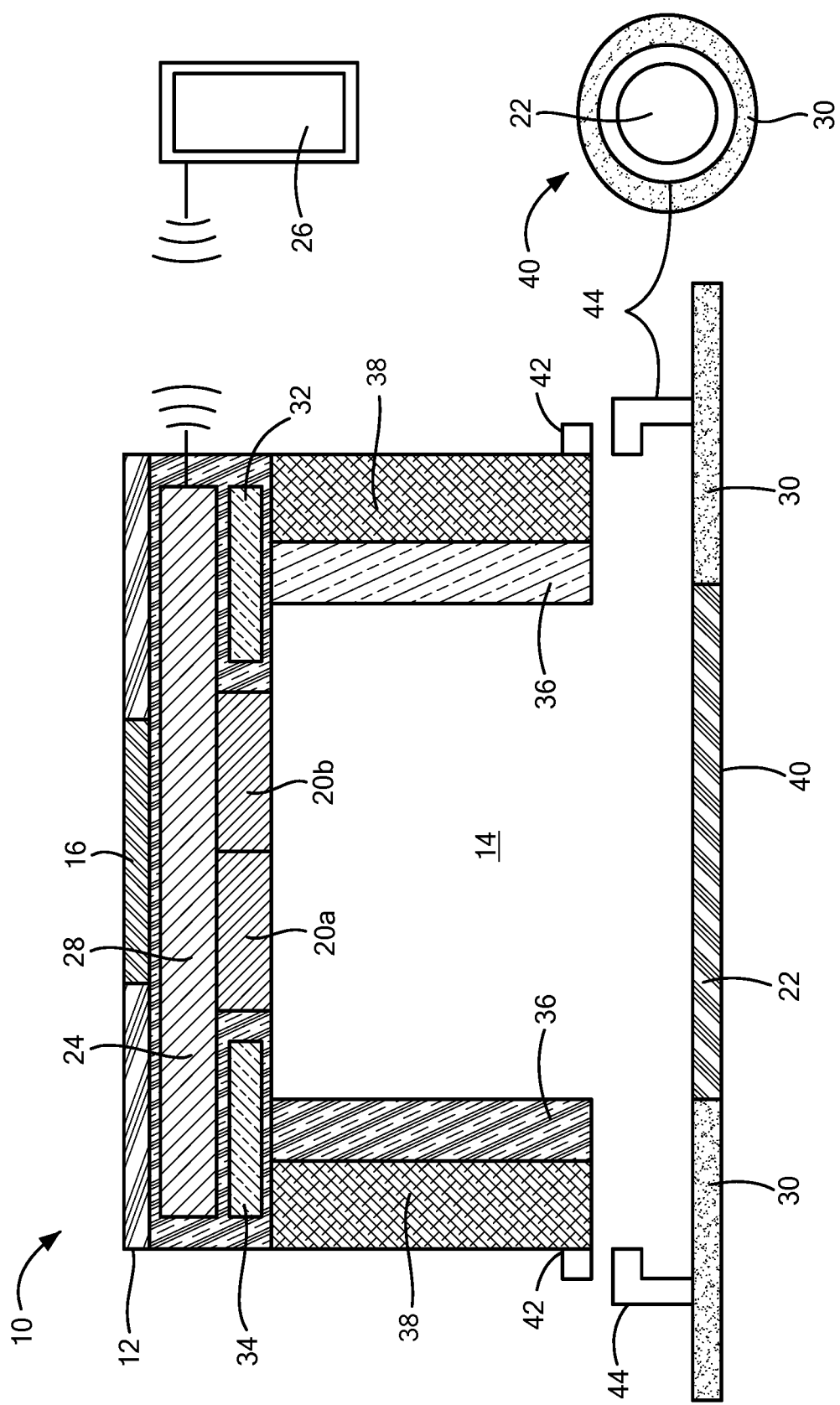
FIG. 11 is another cross-sectional view of embodiment of an acoustic sensor constructed in accordance of the principles of the present application and a top cross-sectional view of a coupling component of the present application.

Referring now to FIG. 11, in this configuration, the TSD 10 includes two internal microphones 20, one external microphone for noise cancelling, a reflectance pulse oximeter 36, a temperature sensor 34, ECG electrodes 38, and an accelerometer 32. The TSD 10 is releasably coupled to a coupling component 40 adhered to the patient's skin with a surrounding area of adhesive tape 30 to releasably connect the TSD 10 to the patient. The coupling component 40 may be adhered to the skin of the neck with the adhesive tape 30 for up to 2 weeks, while the TSD 10 may be removed every few days for recharging. In one configuration, the housing 12 may include a first connector 42, for example, a flange, hook, locking ring or other connectors to releasably couple the housing 12 to a corresponding second connector 44 of the coupling component 40. The adhesive tape 30 may at least partially surround the flexible diaphragm 22 (similar to a pediatric stethoscope head) for attachment to the skin surface of the neck. In one embodiment, the outer surface of coupling component's 40 flexible diaphragm 22 may be coated with an adhesive for robust attachment to the skin surface. Connecting the first connector 42 with the second connector 44 may form a single airtight unit that securely attaches to the skin of the neck above the tracheal notch or lateral to the larynx and excludes ambient sounds. The flexible diaphragm 22 and the bell-shaped chamber may enhance the signal-to-noise ratio of the sound signal measured by the TSD microphones 20. In one embodiment, the second connector 44 may be disposed around the circumference of the diaphragm 22 with the adhesive 30 that mechanically attaches the diaphragm 22 surface to the skin surface. The adhesive tape 30 may further be disposed around the circumference of the flexible diaphragm 22 to firmly secure the coupling component 40 to the skin surface. In another configuration, the center of the adhesive tape 30 may include an open center area between the skin surface and the TSD microphones 20. The open configuration (without a diaphragm) and the bell-shaped stethoscope head may enhance the signal-to-noise ratio of the sound signal measured by the TSD microphone 20.

Although the above embodiments were discussed with respect to medical applications, it is further contemplated that any of the above embodiments may be used in non-medical settings. For example, the AVMS 27 may be used by first responders, whether firefighters, police, EMS, or hazmat teams when encountering potentially dangerous gases, chemicals, or weapons of mass destruction that may affect breathing or acute upper airway obstruction. The AVMS 27 can detect hyperventilation or hypoventilation conditions of first responders which may identify the presence of harmful and potentially dangerous gases or chemicals. In another embodiments, the AVMS 27 may be used to detect low 02 situations such as oil field, breweries, chemical manufacturing facilities, mining operations, dry ice manufacture, food processing and refrigeration/freezing facilities, as well as aviation hypoxia and high altitude; astronauts, space capsules, space suits, etc.

It may be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

What is claimed is:

1. A method of monitoring respiration using an acoustic measurement device, the acoustic measurement device having a sound transducer and an accelerometer, the sound transducer and accelerometer being configured to measure sound vibrations associated with airflow through a mammalian trachea, the method comprising:
   correlating the measured sound vibrations into a measurement of tidal volume;
   calculating at least one selected from the group consisting of absolute tidal volume, a direction of tidal volume, and a rate of change of tidal volume;
   assigning a risk index value to the at least one selected from the group consisting of the absolute tidal volume, the direction of tidal volume, and the rate of change of tidal volume, each risk index value being one selected from a group consisting of a positive score and a negative score based on a predefined scale; and
   generating an alert if the assigned risk index value deviates from a predetermined risk score threshold.

2. The method of claim 1, wherein the measurement of sound associated with airflow through the trachea occurs periodically.

3. The method of claim 1, wherein the acoustic measurement device includes a housing, and wherein the sound transducer is suspended within the housing.

4. The method of claim 3, wherein the housing of the acoustic measurement device has a width between 0.5 cm and 2.5 cm.

5. The method of claim 3, wherein the housing is configured to releasably couple to skin of the mammalian trachea.

6. The method of claim 3, wherein the housing includes a diaphragm configured to vibrate in response to sound.

7. The method of claim 6, wherein the housing is configured to engage a coupling component releasably adhered to the skin, and wherein the coupling component includes the diaphragm.

8. The method of claim 7, wherein the housing includes a connector configured to engage the coupling component.

9. The method of claim 1, wherein the an accelerometer is further configured to measure a relative body position and a movement of the mammal, and wherein the method further includes modifying the respective predetermined range based on the mammal's relative position and movement.

10. The method of claim 1, wherein the acoustic measurement device further includes at least one from the group consisting of a device configured to measure a cardiac electrogram, temperature, and blood oxygenation.

11. The method of claim 1, further including filtering out ambient noise from the measured sound from the trachea.

12. The method of claim 1, wherein the predefined scale includes at least one positive score and at least one negative score.

* * * * *